United States Patent
Balasamy et al.

(10) Patent No.: US 11,103,594 B2
(45) Date of Patent: *Aug. 31, 2021

(54) HIERARCHICAL SILICEOUS MESOSILICALITE NANOCARRIER LOADED WITH PLATINUM(II) COMPLEX

(71) Applicant: Imam Abdulrahman Bin Faisal University, Dammam (SA)

(72) Inventors: Rabindran Jermy Balasamy, Dammam (SA); Sadananda Acharya, Dammam (SA); Vijaya Ravinayagam, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 95 days.

This patent is subject to a terminal disclaimer.

(21) Appl. No.: 15/992,953

(22) Filed: May 30, 2018

(65) Prior Publication Data

US 2019/0231897 A1  Aug. 1, 2019

Related U.S. Application Data

(60) Provisional application No. 62/624,887, filed on Feb. 1, 2018.

(51) Int. Cl.
| | | |
|---|---|---|
| *A61P 35/00* | (2006.01) | |
| *A61K 47/69* | (2017.01) | |
| *A61K 31/282* | (2006.01) | |
| *A61K 9/51* | (2006.01) | |
| *A61K 33/243* | (2019.01) | |
| *B82Y 5/00* | (2011.01) | |

(52) U.S. Cl.
CPC .......... *A61K 47/6923* (2017.08); *A61K 9/51* (2013.01); *A61K 31/282* (2013.01); *A61K 33/243* (2019.01); *A61P 35/00* (2018.01); *B82Y 5/00* (2013.01)

(58) Field of Classification Search
None
See application file for complete search history.

(56) References Cited

U.S. PATENT DOCUMENTS

| | | | |
|---|---|---|---|
| 6,843,977 B2 | 1/2005 | Pinnavaia et al. | |
| 2010/0291387 A1* | 11/2010 | Chaumonnot | C01B 33/46 428/402 |
| 2011/0196285 A1 | 8/2011 | Chen et al. | |
| 2012/0308562 A1 | 12/2012 | Derynck et al. | |

FOREIGN PATENT DOCUMENTS

| | | |
|---|---|---|
| CN | 107303498 A | 10/2017 |
| KR | 10-2006-0013945 | 2/2006 |

OTHER PUBLICATIONS

Munaweera, I., Journal of Inorganic Biochemistry 153: 23-31 (2015). (Year: 2015).*
Mesoporous Materials, obtained from the Internet on Mar. 12, 2020 from https://en.wikipedia.org/wiki/Mesoporous_material. (Year: 2020).*
Taratula, O., et al., Journal of Drug Targeting 19(10): 900-914 (2011). (Year: 2011).*
Dr. Christine E. A. Kirschhock, et al. ; Design and Synthesis of Hierarchical Materials from Ordered Zeolitic Building Units ; Jul. 18, 2005 ; Abstract ; http://onlinelibrary.wiley.com/doi/10.1002/chem.200401329/abstract.
Yoo Wo Cheol, et al. ; Synthesis of mesoporous ZSM-5 zeolites through desilication and re-assembly processes ; Feb. 1, 2012 ; Abstract ; https://www.sciencedirect.com/science/article/pii/S1387181111003660.
Dr. Zongtao Zhang ; Strongly Acidic and High-Temperature Hydrothermally Stable Mesoporous Aluminosilicates with Ordered Hexagonal Structure ; Apr. 1, 2001 ; Abstract ; http://onlinelibrary.wiley.com/doi/10.1002/1521.

* cited by examiner

*Primary Examiner* — David J Blanchard
*Assistant Examiner* — Daniel F. Coughlin
(74) *Attorney, Agent, or Firm* — Oblon, McClelland, Maier & Neustadt, L.L.P.

(57) ABSTRACT

A platinum(II) complex loaded on a mesosilicalite nanocarrier having a hierarchical silicalite characterized by a molar ratio of aluminum to silica in a range of 1:3000 to 1:1000. The hierarchical silicalite includes mesopores of a hexagonal structure, and micropores of silicalite structure with a microporous volume in the range of 0.05 cc/g to 0.1 cc/g. The mesosiliclite nanocarrier loaded with the platinum(II) complex is suitable for treatment of cancer, in particular, breast, cervical, and colon cancers.

12 Claims, 17 Drawing Sheets

HIERARCHICAL SILICEOUS MESOSILICALITE NANOCARRIER LOADED WITH PLATINUM(II) COMPLEX

CROSS-REFERENCE TO RELATED APPLICATION

This application claims priority benefit from provisional application 62/624,887, filed Feb. 1, 2018.

BACKGROUND OF THE INVENTION

Technical Field

The present invention relates to a hierarchical mesosilicalite nanocarrier loaded with platinum(II) complexes, a method for making the hierarchical mesosilicalite nanocarrier and its use for the treatment of cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Platinum(II) complexes, in particular, cisplatin are among the most effective anticancer drugs as they have excellent cytotoxic activities. They, however, suffer from several drawbacks. Cancers treated with platinum(II) complexes develop drug resistance, and the patients suffer from undesirable side effects including peripheral neuropathy, nephrotoxicity, hearing loss, nausea, and associated pain. Although some platinum(II) complexes such as carboplatin and oxaliplatin have reduced toxicity with reasonable anticancer activity, the replacement of chloride ligands of cisplatin decreases the chemotherapeutic efficacy of the platinum(II) complex leading to the use of larger doses, and hence significantly increases the cost of treatment [Jung et al. "Direct Cellular Responses to Platinum-Induced DNA Damage" *Chemical Reviews* 2007, 107, 1387-1407]. Many attempts to identify cisplatin analogs having the desired clinical efficacy while avoiding or minimizing the side effects have failed [Eckardt et al. "Phase II study of picoplatin as second-line therapy for patients with small-cell lung cancer" *J. Clin. Oncol.* 2009, 27, 2046-2051]. Cisplatin associated drug formulation is reported to have a major role in determining the cytotoxicity cisplatin. Dimethyl sulfoxide (DMSO) deactivates the anticancer activity of cisplatin due to platinum complexation with the solvent, whereas dimethylformamide (DMF) enhances the cytotoxicity of cisplatin [Hall et al. "Dimethyl sulfoxide Inactivates Cisplatin, Carboplatin and Other Platinum Complexes. *Cancer Res.* 2014, 74(14), 3913-3922].

Nanocarriers have been shown to reduce the side effects of anticancer drugs by selectively targeting tumor through enhanced permeability and retention and thereby reduce the effective dose of the drug and minimize the exposure of normal cells to the cytotoxicity of the drug. Numerous types of nanocarriers involving polymer based micelles of different chain lengths and nanofibers for cisplatin loading have been studied. For instance, cisplatin loaded over epidermal growth factor formulated with polyethylene glycol-polylactic-co-glycolic acid-polylysine through double emulsion technique is shown to reduce the toxicity and enhance the anticancer activity in human ovarian adenocarcinoma cell line [Wang et al. Toxicity and therapy of cisplatin-loaded EGF modified mPEG-PLGA-PLL nanoparticles for SKOV3 cancer in mice, *Biomaterials* 2013, 34, 4068-4077]. Nanofibers with high textural characteristics such as high surface area, strong bio-adhesiveness, and high loading capabilities are reported to be effective for cisplatin loading. In a multistep synthesis protocol, preparation of polymeric solution containing polycaprolactone, dichloromethane, DMF and chitosan is reported. Dissolution in DMF using electrospinning technique is shown to be effective for cisplatin loading in PLGA [poly(lactic-co-glycolic acid)] nanoparticles [Parhizkar et al. "Electrohydrodynamic encapsulation of cisplatin in poly(lactic-co-glycolic acid) nanoparticles for controlled drug delivery" *Nanomedicine: Nanotechnology, Biology, and Medicine* 2016, 12, 1919-1929]. The PLGA encapsulated 70 wt. % of cisplatin and loaded up to 10 wt. % of cisplatin using dimethylacetamide solvent and electrohydrodynamic atomization (electro spray) technique with electric potential voltage of 12-20 kV. Other effective polymeric carriers of cisplatin have been reported. Developing a large scale production method for nanomedicine requires minimizing the challenges presented by multiplicity of steps in a method, the usage of several solvents, and stability of the polymeric template.

Nanoporous silica based drug delivery systems have attracted interest as drug carriers. In comparison to other drug carriers such as capsules, viruses and liposomes, the nanosilica is biocompatible and stable in biological environment. Mesosilica nanoparticles with surface carboxyl groups bind oxaliplatin. The bound oxiplatin to mesosilica displays high cytotoxicity against HepG2 cell line [He et al. "Synthesis porous silica nanoparticle-oxaliplatin conjugates for improved anticancer drug delivery" *Colloids and Surfaces B: Biointerfaces* 2014, 117, 75-81]. The synthesis of hollow type mesoporous silica functionalized with carboxyl group was reported as an efficient drug delivery platform for cisplatin. Carboxylic group functionalized hollow mesoporous silica nanospheres synthesized in the presence of polystyrene spheres templates have large surface area for loading cisplatin (~48%) [Farsangi et al. "One-pot controllable synthesis of carboxylic group functionalized hollow mesoporous silica nanospheres for efficient cisplatin delivery" Z. *RSC Adv.* 2016; 6, 67592-67598]. Mesoporous silica coordinated with photosensitizer aluminum chloride phthalocyanine and cisplatin in DMSO was an effective therapy for human cervical cancer. In particular, synergetic effect of photosensitizer and cisplatin was more toxic against HeLa cells than cisplatin-silica combination [Vivero-Escoto et al. "Mesoporous Silica Nanoparticles Loaded with Cisplatin and Phthalocyanine for Combination Chemotherapy and Photodynamic Therapy in vitro" *Nanomaterials* 2015, 5, 2302-2316]. The core shell concept of super paramagnetic Fe3O4 based mesoporous silica functionalized with carboxylic functional group are reported to be effective for cisplatin loading and controlled release. The nanocomposite formed by condensation of a silica source with carboxyethylsilanetriol sodium followed by the addition of carboxyl functional groups was reported to encapsulate cisplatin in aqueous DMSO and have anticancer activity against cancer cell lines A549 and MCF-7 [Zhu et al. "Magnetic core-mesoporous shell nanocarriers with drug anchorages suspended in mesopore interior for cisplatin delivery" *Micropore Mesopore Mat.* 2014, 196, 115-121]. It should be noted that the reported MCM-41 based nanocarriers have an amorphous framework structure, where drug release is controlled by several factors including derivatization, pore size, and the constraint imposed on diffusion by the pore nanostructure [Shen et al. "Physical state and dissolution ibuprofen formulated by co-spray drying with mesoporous silica: effect of pore and particle size. *Int. J. Pharm.* 2011, 410, 188-195; and Saha et al. "Controlled release of antipyrine from mesoporous carbons, *Micropor and Mesopor. Mater.* 2014, 196, 327-334]. Also, pharmaceutical industrial scale up of a formulation with pure mesoporous MCM-41 phase was limited due the poor hydrothermal and steam stability.

In recent years, various techniques have been applied to improve the nanosilica stability and accessibility of the pores of MCM-41. Recently, the synthesis of hierarchical porous silicalite materials using zeolite seed based hexagonal mesophase through top-down and bottom-up approach was described [Jermy, B. R. "Synthesis of hexagonal aluminosilicate from liquid-crystalline mesophase using zeolitic nanoclusters: bottom-up versus top-down approach, *J Porous Mater* 2017]. The top-down approach involves preparation of hierarchical porous materials by disintegrating a fully grown zeolite such as silicalite or ZSM-5 or other zeolites in presence of a mesotemplate, while the bottom-up approach involves building up of mesoporous materials through zeolitic seed solution derived from basic chemical ingredients. The presence of a crystalline framework in SiMCM-41 mesophase would be highly advantageous for multifunctional therapeutics. Moore recently, hierarchically structured mesoporous silica (ZSM-5/MCM-41) with zeolitic ZSM-5 and mesoporous MCM-41 interlinked domains has been used as catalyst in the petrochemical industry. It has been reported that primary or secondary zeolitic building units of nano zeolitic seeds in the synthesis of gel increases the framework crystallinity of MCM-41 [Odedairo et al. "Aromatic transformation over ZSM-/MCM-41 composites with adjustable porosity in fluidized bed reactor, *Catal. Sci. Technol.,* 2012, 2, 1275-1286; and Balasamy et al. Unique catalytic performance of mesoporous molecular sieves containing zeolite units in transformation of m-xylene" *Appl. Catal. A: Gen.* 2011, 409-410, 223-233].

It is therefore one objective of the present disclosure to provide a nanocarrier-loaded anticancer complex and a method for making the complex. The present disclosure describes the preparation of platinum(II) complexes/mesosilicalite nanoformulations. In particular, a cisplatin/mesosilicalite nanoformulation type designated as IAUM-56 (Imam Abdulrahman Bin Faisal University Mesosilicalite-56) was shown to be effective for cancer therapy. The silicalite is the silicate form of ZSM-5 and contains no aluminum in the framework and has little, if any, toxic effect. The siliclite formulation of cisplatin imparts stability to amorphous framework of SiMCM-41. The cisplatin/mesosilicalite nanoformulation of the present disclosure effectively inhibited the growth of cervical cancer Hela cells and breast cancer MCF7 cells.

SUMMARY OF THE INVENTION

A first aspect of the invention is directed to mesosilicalite nanocarriers comprising a hierarchical silicalite having silica to aluminum molar ratio in a range of 1000:1 to 3000:1, comprising:
a mesophase with mesopores of a hexagonal structure; and
a microphase with micropores of a microporous volume in the range of 0.05 cc/g to 0.1 cc/g; and
a platinum(II) complex loaded in mesopore and micropore of the nanocarrier;
wherein a mean pore diameter of the mesosilicalite nanocarrier in the range of 1.5 nm to 5.5 nm.

In a preferred embodiment, the platinum(II) complex is at least one selected from the group consisting of cisplatin, carboplatin, oxaliplatin, nedaplatin, triplatin tetranitrate, phenanthriplatin, picoplatin, and strataplatin.

In another preferred embodiment, the mesosilicalite nanocarrier comprises platinum(II) complex in the range of 0.001 to 1.0 mmol/g of the total weight of the mesosilicalite nanocarrier, more preferably in the range of 0.01 to 0.5 mmol/g of the total weight of the mesosilicalite nanocarrier.

In another preferred embodiment, the mesosilicalite nanocarrier comprises at least one small group of pores having a pore dimeter in the range of about 2.1 to 3.0 nm, more preferably in the range of about 2.2 to 2.7 nm, and most preferably of about 2.3 to 2.5 nm. Also, the mesosilicalite nanocarrier comprises at least a second larger group of pores having a dimeter in the range of about 3.4 to 4.0 nm, preferably in the range of about 3.6 to 3.9 nm, more preferably in the range of about 3.7 to 3.8 nm.

In another preferred embodiment, the BET surface area of mesosilicalite nanocarriers is in the range of about 400 to about 1400 $m^2/g$, and more preferably in the range of about 600 to 1000 $m^2/g$.

In another preferred embodiment, the total pore volume of the mesosilicalite nanocarriers is in the range of about 0.30-0.90 mL/g, and and most preferably of in the range of about 0.53 to 0.77 mL/g.

A second aspect of the invention is related to a method of making mesosilicalite nanocarriers loaded with platinum(II) complex comprises:
mixing hierarchical mesosilicalite nanocarriers having silica to aluminum molar ratio in a range of 1000:1 to 3000:1 with a platinum(II) complex dissolved in aqueous salt solution, isolating the mesosilicalite nanocarrier loaded with the platinum complex.

A preferred embodiment of the method wherein the platinum(II) complex is cisplatin, carboplatin, oxaliplatin, nedaplatin, triplatin tetranitrate, phenanthriplatin, picoplatin, or strataplatin. In a more preferred embodiment, the platinum(II) complex is cisplatin, carboplatin, oxaliplatin, and nedaplatin. In the most preferred embodiment, the platinum(II) complex is cisplatin.

Another preferred embodiment the salt solution is 0.9% sodium chloride in water. Another preferred embodiment of the method, the concentration of the platinum(II) complex concentration in solution is in the range of 1.0 mM to 20.0 mM.

A third aspect of the invention is related to a pharmaceutical composition comprising the mesosilicalite nanocarriers loaded with a platinum(II) complex described herein.

A preferred embodiment, the pharmaceutical composition comprises the mesosilicalite nanocarriers loaded with a platinum(II) complex in the range of 0.001 to 1.0 mmol/g of a nanocarrier.

Another preferred embodiment, the pharmaceutical composition comprises the mesosilicalite nanocarriers loaded in the range of 0.011 mmol to 0.9 mmol of platinum(II) complex per gram of mesosilicalite nantocarrier.

Another preferred embodiment, the pharmaceutical composition comprises the mesosilicalite nanocarriers loaded with at least one platinum(II) complex selected from the group consisting of cisplatin, carboplatin, oxaliplatin, nedaplatin, triplatin tetranitrate, phenanthriplatin, picoplatin, and strataplatin.

A preferred embodiment, the pharmaceutical composition comprises 0.1-400 μM of the platinum(II) complex relative to the total volume of the composition.

Another preferred embodiment, the pharmaceutical composition further comprises at least one more chemotherapeutic agent.

Another preferred embodiment, the pharmaceutical composition comprises one or more carrier and/or excipient selected from the group consisting of a buffer, an inorganic salt, a fatty acid, a vegetable oil, a synthetic fatty ester, a surfactant, a sugar, a polymer, and combination thereof.

A fourth aspect of the invention is related to a method for treating a proliferative disorder, comprising administering to a subject in need of therapy an effective amount of a pharmaceutical composition described herein.

Another preferred embodiment of the method, the cancer subject in need of therapy an effective amount of a pharmaceutical composition described herein is at least one selected from the group consisting of ovarian cancer, cervical cancer, testicular cancer, colon cancer, bladder cancer, breast cancer, non-small cell lung cancer, esophageal cancer, endometrial cancer, head and neck cancer, osteogenic sarcoma.

A more preferred embodiment of the method of treatment, the cancer is cervical cancer, breast cancer, or colon cancer.

Another preferred embodiment of the method of treatment, the proliferative disorder is a tumor.

Another preferred embodiment of the method, the subject of treatment is an animal, more preferably a mammal, and most preferably human.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
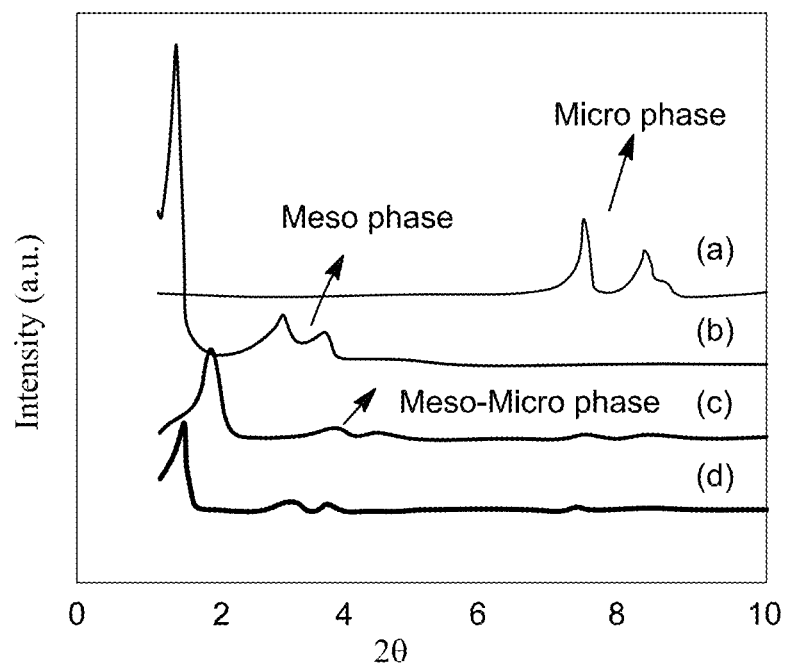
FIG. 1A shows a low angle XRD diffraction of a silicalite, lines (a) and (b) show the low angle XRD diffraction of silicalite and conventional SiMCM-41, respectively. Lines (c) and (d) show the diffractions of the synthesized hierarchical mesosilicalite and calcined mesosilicalite, respectively.

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the terms "compound" and "complex" are used interchangeably, and are intended to refer to a chemical entity, whether in a solid, liquid or gaseous phase, and whether in a crude mixture or purified and isolated.

Unless otherwise specified, "a" or "an" means "one or more".

As used herein, the term "salt" refers to derivatives of the disclosed compounds wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein, the term "solvate" refers to a physical association of a compound, monomer or polymer of this disclosure with one or more solvent molecules, whether organic or inorganic. This physical association includes hydrogen bonding. In certain instances, the solvate will be capable of isolation, for example when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those of ordinary skill in the art.

As used herein a "polymer" or "polymeric resin" refers to a large molecule or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer or resin whose repetition would produce the complete polymer chain (excluding the end groups) by linking the repeating units together successively along the chain. The method by which monomers combine end to end to form a polymer is referred to herein as "polymerization" or "polycondensation", monomers are molecules which can undergo polymerization, thereby contributing constitutional repeating units to the structures of a macromolecule or polymer. As used herein "resin" or "polymeric resin" refers to a solid or highly viscous substance or polymeric macromolecule containing polymers, preferably with reactive groups. As used herein a "copolymer" refers to a polymer derived from more than one species of monomer and are obtained by "copolymerization" of more than one species of monomer. Copolymers obtained by copolymerization of two monomer species may be termed bipolymers, those obtained from three monomers may be termed terpolymers and those obtained from four monomers may be termed quarterpolymers, etc. As used herein, "cross-linking", "cross-linked" or a "cross-link" refers to polymers and resins containing branches that connect polymer chains via bonds that link one polymer chain to another.

The cross-link may be an atom, a group of atoms, or a number of branch points connected by bonds, groups of atoms, or polymer chains. In the majority of cases, a cross-link is a covalent structure or covalent bond but the term may also describe sites of weaker chemical interactions, portion crystallites, and even physical interactions and entanglements. The cross-linking can alter the physical and mechanical properties of the polymer. Cross-linking may be formed by chemical reactions that are initiated by heat, pressure, change in pH, and/or radiation, with or without the presence of a cross-linking agent and/or catalyst. In certain embodiments, at least one diaminoalkane a cross-linking agent for the cross-linked polymeric resin described herein.

The terms "mesosilicalite nanocarrier" and "nanocarrier" have the same meaning and are used interchangeably throughout the disclosure.

According to a first aspect, the present disclosure relates to a mesosilicalite nanocarrier having a hierarchical silicalite loaded with platinum(II) complex wherein the mesosilicalite nanocarrier is characterized by a molar ratio of silica to aluminum in a range of 1000:1 to 3000:1, or 1500:1 to 2500:1. The preparation of the nanocarrier is described in copending application U.S. Ser. No. 15/478,794, which is incorporated herein in its entirety by reference, and can be prepared using siliclite or other high silica medium or large zeolites such as, but not limited to, ZSM-5, mordenite, Beta, YH, ZSM-11, ZSM-12, ZSN-22, and ZSM-23.

Silicalite is a polymorph of silica having a structure analogous to zeolite. The hierarchical silicalite includes mesopores of a hexagonal structure, and micropores. The mesopores have a volume in the range of 0.11 cc/g to 1.5 cc/g, preferably in the range of 0.15 cc/g to 1.25 cc/g, more preferably in the range of 0.25 cc/g to 1 cc/g, and most preferably in the range of 0.5 cc/g to 0.75 cc/g. The micropores have a volume in the range of 0.05 cc/g to 0.1 cc/g, preferably in the range of 0.06 cc/g to 0.09 cc/g, and more preferably in the range of 0.07 cc/g to 0.08 cc/g. The nanocarrier exhibits a hexagonal mesoporous form and silicalite form. The mesopores and micropores for the nanocarrier characterize the hierarchical structure of the mesosilicalite, wherein the mesopores form the mesophase and the micropores form the microphase. The relative weight ratios of these two phases approximate the relative weight ratios of the SiMCM-41 and silicalite used in the synthesis. The micropore diameter is in the range of about 2.0 to 2.8 nm, preferably in the range of about 2.2 to 2.6 nm, more preferably in the range of about 2.3 to 2.4. The mesopore diameter is in the range of about 2.9 to 4.0 nm, preferably in the range of 3.2 to 3.9 nm, more preferably in the range of about 3.5 to 3.8nm, and most preferably in the range of about 3.8 to 3.9 nm. The hierarchy of the mesophase and microphase results in improved interaction with materials that can be carried, adsorbed, absorbed and/or otherwise contacted by the nanocarrier due to a greater surface area of contact with two phases instead of one phase, and an improved flow, or exchange, of the materials that may be carried into and out of the nanocarrier.

The nanocarrier carrier may be loaded with any platinum (II) complex effective for the treatment of cancer. Many platinum(II) complexes are well-known in the art and used in treatment of cancer including, but not limited to, cisplatin, carboplatin, oxaliplatin, nedaplatin, triplatin tetranitrate, phenanthriplatin, picoplatin, or strataplatin and one or more may be loaded on the nanocarrier of the present disclosure. In a preferred embodiment, the platinum(II) complex is at least one of cisplatin, carboplatin, oxaliplatin, and nedaplatin.

According to the second aspect of the invention is related to a method of preparing mesosilicalite nanocarriers loaded with a platinum(II) complex. Platinum(II) complexes may be loded on any nanocarriers such as but not limited to mesosilicalite nanocarrier, metal oxide incorporated ZSM-5 such as TiZSM-5, mesocarbon, graphene oxide, and metal organic frame work.

The platinum(II) complex is preferably loaded into the mesosilicalite nanocarrier by the equilibrium adsorption method. The method may take place in a sequence of steps in which a solution of a platinum(II) complex solution is contacted with the mesosilicalite nanocarrier until no net transfer between the mesosilicalite nanocarrier and the platinum(II) complex solution is observed. The transfer may be continuously monitored by FTIR spectra which display characteristic signals of the loaded platinum(II) complex. The combination of micropores and mesopores of the presently described mesosilicalite nanocarrier exhibited higher payload capacity of platinum(II) complex than that of the parent silicalite and SiMCM-41 in the following order: mesosilicalite nanocarrier>SiMCM-41>silicalite.

In a preferred embodiment, the method comprises: mixing hierarchical mesosilicalite nanocarriers having silica to aluminum molar ratio in a range of 1000:1 to 3000:1 with a platinum(II) complex dissolved in a salt solution. The mixture is stirred or agitated in ice bath temperature in the dark until the white mixture becomes light yellow. Then, the hierarchical mesosilicalite nanocarriers loaded with the platinum(II) complex are filtered and air dried.

Any platinum(II) complex suitable for the treatment of cancer may be used in the method to prepare the Pt(II) complex loaded nanocarrier. In a preferred embodiment of the method the platinum(II) complex is one or more of cisplatin, carboplatin, oxaliplatin, nedaplatin, triplatin tetranitrate, phenanthriplatin, picoplatin, or strataplatin. In a more preferred embodiment, the platinum(II) complex is one or more of cisplatin, carboplatin, oxaliplatin, and nedaplatin. In the most preferred embodiment, the platinum (II) complex is cisplatin.

In another preferred embodiment of the method, the concentration of the platinum(II) complex concentration in solution is in the range of 0.10 to 50 mM , more preferably in the range 0.05 to 30.0 mM, and most preferably 1.0 mM to 20.0 mM. In a particularly preferred embodiment, the platinum(II) complex concentration in solution is in the range of about 3.0 to 10 mM.

The amount of nanocarrier mixed with the platinum(II) solution may vary depending on the desired loading of the platinum(II) complex and the scale of preparation. In some embodiments the nanocarrier is added in the range of about 1.0 to 300 mg of nanocarrier per mL of the platinum(II) complex solution, preferably in the range of about 2.0 to 200 mg of nanocarrier per mL of the platinum(II) complex solution, more preferably in the range of about 3.0 to 100 mg of nanocarrier per mL of the platinum(II) complex solution, and most preferably in the range of about 3.0 to 60 mg of nanocarrier per mL of the platinum(II) complex solution.

Another preferred embodiment of the method, the salt is alkali or alkaline earth metal salt or ammonium salts. Examples of salts include but not limited to sodium or potassium chloride, bromide, carbonate, bicarbonate, nitrate, sulfate, acetate, tartrate, citrate; or ammonium chloride, bromide, carbonate, or bicarbonate. The salt concentration in the solution is in the range of about 0.1% to 2.0%, preferably in the range of 0.3% to 1.5%, more preferably in the range of 0.5% to 1.3%, and most preferably in the range of 0.8% to 0.9%.

Another preferred embodiment of the method, the salt solution is a water solution or a mix organic water solution.

A third aspect of the invention is related to a pharmaceutical composition comprising the mesosilicalite nanocarrier loaded with the platinum(II) complex described herein.

As used herein, a "composition" or a "pharmaceutical composition" refers to a mixture of the active ingredient with other chemical components, such as pharmaceutically acceptable carriers and excipients. One purpose of a composition is to facilitate administration of the nanocarrier loaded with platinum(II) complex of the invention to a subject. Pharmaceutical compositions of the present disclosure may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the nanocarrier loaded with platinum(II) complex which may comprise a salt, a solvate, or any mixtures thereof.

A preferred embodiment, the pharmaceutical composition comprises the mesosilicalite nanocarriers loaded with a platinum(II) complex in the range of 0.001 to 1.80 mmol/g based on the total weight of the nanocarrier, more preferably in the range of 0.0025 to 1.50 mmol/g of nanocarrier, even more preferably in the range of 0.05 to 1.20 mmol/g of nanocarrier, and most preferably 0.01 to 0.9mmol/g of nanocarrier.

In a particularly preferred embodiment, the pharmaceutical composition comprises the mesosilicalite nanocarrier loaded with about 0.011 mmol or 0.9 mmol of the platinum (II) complex per gram of nanocarrier.

In another preferred embodiment, the pharmaceutical composition comprises the mesosilicalite nanocarrier loaded with one or more platinum(II) complexes such as, but not limited to, cisplatin, carboplatin, oxaliplatin, nedaplatin, triplatin tetranitrate, phenanthriplatin, picoplatin, or strataplatin. In a more preferred embodiment, the loaded platinum (II) complex is selected from the group consisting of cisplatin, carboplatin, oxaliplatin, and nedaplatin. In the most preferred embodiment, the loaded platinum(II) complex is cisplatin.

In one or more embodiments, the pharmaceutical composition comprises at least 0.1 wt. %, 0.5 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, 95 wt. %, 99 wt. %, or 99.9 wt. % of the nanocarrier loaded with the platinum(II) complex relative to the total weight of the pharmaceutical composition. In some embodiments, the pharmaceutical composition comprises up to 0.1 wt. %, 1 wt. %, 5 wt. %, or 10 wt. % of a pharmaceutically acceptable salt. In some embodiments, the pharmaceutical composition comprises up to 0.1 wt. %, 0.5 wt. %, 1.0 wt. %, 2.0 wt. %, 3.0 wt. %, 4.0 wt. %, 5.0 wt. %, or 10.0 wt. % of a pharmaceutically acceptable solvate. Preferably, the pharmaceutical composition may further comprise pharmaceutically acceptable binders, such as sucrose, lactose, glucose, fructose, galactose, mannitol, xylitol, and pharmaceutically acceptable excipients such as calcium carbonate and calcium phosphate.

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used. In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HRS, and C-4I, ovarian cancer cell lines, e.g., A2780, A2780cis, OV7, and PE023, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, cervical cancer, testicular cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

In a preferred embodiment, the pharmaceutical composition comprises 0.1-400 µM of the platinum(II) complex relative to the total volume of the composition.

In another preferred embodiment, the pharmaceutical composition comprises one or more carriers and/or excipients selected from the group consisting of a buffer, an inorganic salt, a fatty acid, a vegetable oil, a synthetic fatty ester, a surfactant, a sugar, a polymer, and combination thereof.

In another preferred embodiment, the pharmaceutical composition may comprise other active ingredients in addition to the nanocarrier loaded with the platinum(II) complex. In one embodiment, the other active ingredient may be a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The anticancer agent is preferably at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)-dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl-ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having the nanocarrier loaded with a platinum(II) complex disclosed herein thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about one hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least one hour following oral administration. In another embodiment, controlled-release results in substantially complete dissolution after at least one hour following rectal administration. In one embodiment, the composition is not a controlled-release composition.

A fourth aspect of the invention is related to a method for treating a proliferative disorder, comprising administering to a subject in need of therapy an effective amount of a pharmaceutical composition comprising the mesosilicalite nanocarriers containing the platinum(II) complex, wherein the proliferative disorder is cancer and/or tumor.

As used herein, the terms "treat", "treatment", and "treating" in the context of the administration of a therapy to a subject in need thereof refers to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the fourth aspect is for treating cancer of the blood, brain, bladder, lung, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, cervical cancer, breast cancer, and lung cancer. In a more preferred embodiment, the cancer is cervical cancer or breast cancer. In the most preferred embodiment, the cancer is cervical cancer or breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary nonpolyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In one or more embodiments, the pharmaceutical composition administered comprises the nanocarrier loaded with platinum(II) complex.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the mesosilicalite nanocarriers loaded with the platinum(II) complex per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing the nanocarriers loaded with platinum(II) complex of the current disclosure as a single dose or multiple individual divided doses. In some embodiments, the composition is administered at various dosages (e.g. a first dose with an effective amount of carrier comprising 200 mg of the platinum(II) complex per kilogram of the subject and a second dose with an effective amount of carrier comprising 50 mg of the platinum(II) complex per kilogram of the subject). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MM, DCE-MRI and PET scan.

In most embodiments of treatment, the method further comprises measuring a concentration of a biomarker and/or detecting a mutation in a biomarker before and/or after the pharmaceutical composition comprising the nanocarrier loaded with the platinum(II) complex of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the nanocarrier loaded with the platinum(II) complex by at least 5%, at least 10%, or at least 30%, up to 50%, up to 60%, or up to 80% of an initial effective amount nanocarrier loaded with platinum(II) complex that contains in the range of 1-300 mg of the platinum(II) complex per kilogram of the body weight of the subject. The increased effective amount may be in a range of 1.05-540 mg/kg, preferably 15-420 mg/kg, more preferably 25-270 mg/kg. The subject may be administered with the increased dosage for a longer period (e.g. one more week, 2 more weeks, or 2 more months) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The foregoing paragraphs have been provided by way of general introduction, and are not intended to limit the scope of the following claims. The described embodiments, together with further advantages, will be best understood by reference to the following detailed description taken in conjunction with the accompanying drawings.

EXAMPLE 1

Methods:
Characterization: The X-ray diffraction patterns for mesostructured silicas were obtained on a bench top Rigaku Multiplex system. The textural characteristics including surface area, pore volume and pore size distribution were measured on an ASAP-2020 plus, and accelerated surface area and porosity were determined on Micromeritics, Norcross, Ga., USA. The cisplatin/hierarchical silicalite solid samples were measured using 60 mm diameter integrating sphere equipped UV-Vis V-750 diffuse reflectance spectroscopy (JASCO). The cisplatin functional groups were identified using Fourier transform infrared spectroscopy (Perkin Elmer) equipped with attenuated total reflectance (ATR). Surface morphologies were measured using transmission electron microscope (TEM, FEI, Morgagni, Czec Republic). TEM samples were prepared by dropping particle dispersions onto carbon-coated Cu grids and air-dried before mounting on the microscope. Particle sizes were determined from electronic images using Gatan digital micrograph software. The data is presented in the form of average number for each specimen with standard deviation.

Drug Release:
For drug release study, cellulose membrane (MWCO=14,000) dialysis tubing was used to study the drug release at pH 5.0. The dialysis bags were treated with 100 ml PBS solution for 30 min. IAUM-56 (30 mg) was mixed with 3 ml of PBS, pH 5.0, in the treated dialysis bag. Then, the dialysis bag was inserted in 100 ml beaker containing 47 ml of PBS at 37° C. and the amount of drug released from the bag was determined.

LC50s are calculated by ComuSystem utilizing the median-effect equation: $Fa/Fu=(D/Dm)^m$ equation, where Fa is the observed fraction affected and Fu=1-Fa, D is the dose of the drug, and Dm is the LC50. Thus, a plot of log Fa/Fu vs Log D is linear and the intercept with the X axis is LC50.

EXAMPLE 2

Designing Nanocarrier:

Silicalite with particle size 1-5 nm is prepared by similar method to that described in U.S. patent application Ser. No. 15/478,794 which is incorporated herein in its entirety by reference using Ludox AS-40 and TPABr as silica and templating agent, respectively. The formation of mesosilicalite occurred through alkaline dissolution in 0.7M NaOH in the presence of meso phase inducing template cetyltrimethylammonium bromide (CTAB) for 24 h. Then, the solution pH was adjusted to pH 9, stirred, and hydrothermally treated at 100° C. for 24 h. The obtained milky solution is cooled, filtered, washed, dried and calcined at 550° C. for 6 h.

EXAMPLE 3

Preparation of Nanocarrier Loaded with Cisplatin:
(a) Cisplatin loading of 0.011 mmolg-1 nanocarrier in normal saline solution (NSS): Cisplatin (15 mg) was added to 5 ml of saline solution. After dissolution, activated mesosilicalite or SiMCM-41 (300 mg) was added and left in an ice cooled bath with stirring in the dark. The transformation of white solution to light yellow was observed during stirring. Then, the solution was filtered, washed, and dried at room temperature. The filtered product was stored at 4° C. The filtrate and washed saline was collected and the amount of cisplatin loaded on the nanocarrier was determined spectrophotometrically at 208 nm.
(b) Cisplatin loading of 0.9 mmolg-1 nanocarrier in NSS solution: Cisplatin (13.5 mg) was dissolved in 15 ml of NSS solution and after dissolution, activated mesosilicalite or SiMCM-41 (50mg) was added and stirred for 24 h in an ice cooled dark environment. After stirring, the solution mixture was filtered, washed, dried at room temperature and stored at 4° C. The cisplatin loading was determined as described above.
(c) Cisplatin loading (0.9 mmolg-1 nanocarrier) in DMSO solution: Cisplatin (13.5 mg) was dissolved in 15 ml of DMSO (3 mM solution) and after dissolution, activated mesosilicalite or SiMCM-41 (50 mg) was added and stirred for 24 h in an ice cooled dark environment. After stirring, the solution mixture was filtered, washed, dried at room temperature and then stored at 4° C. The cisplatin loading was determined as described above.

EXAMPLE 4

Figure 1B:
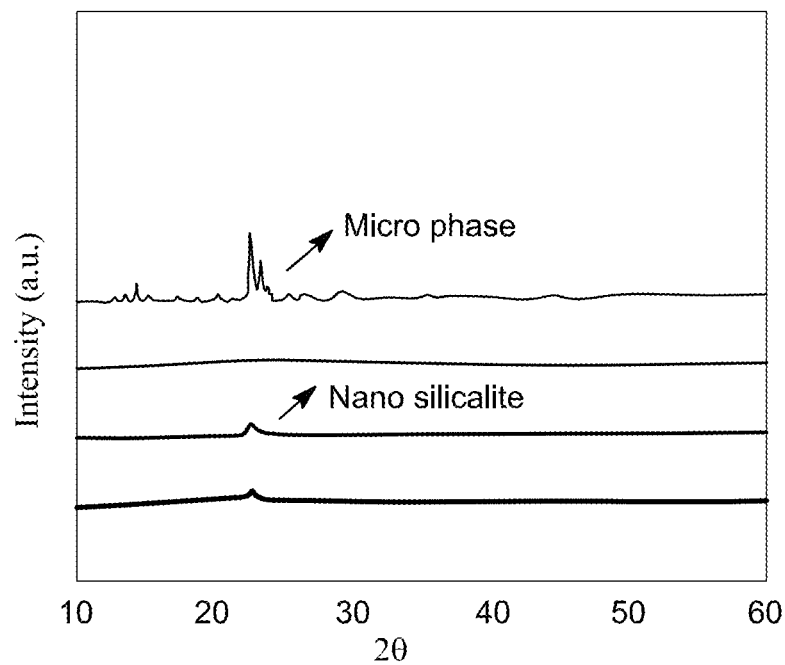
FIG. 1B shows high XRD diffraction from top to bottom silicalite, conventional SiMCM-41, the synthesized mesosilicalite, and calcined mesosilicalite.
Figure 1C:
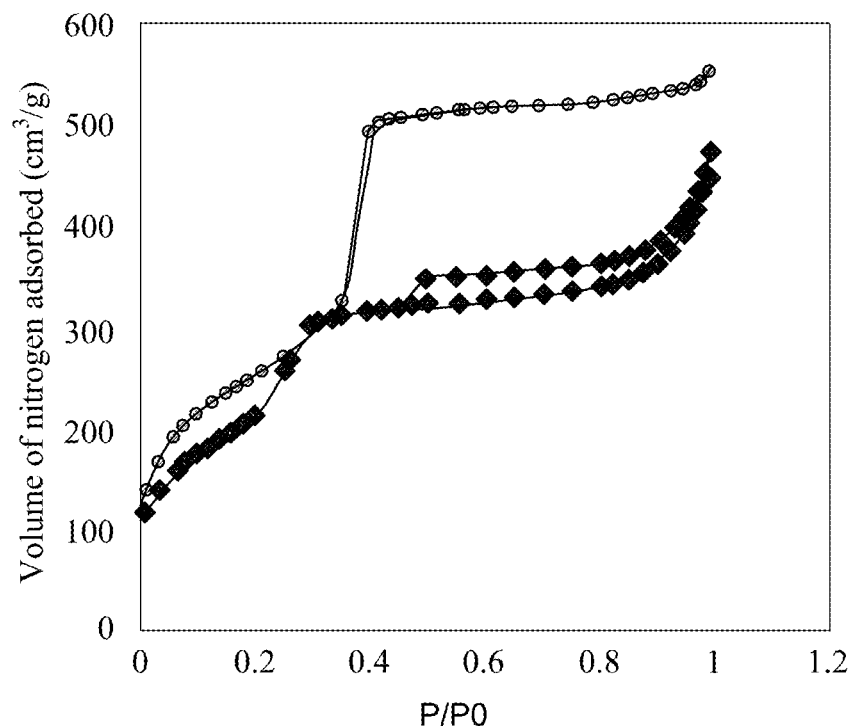
FIG. 1C shows nitrogen adsorption isotherm of mesosilicalite prepared using 0.7M NaOH treatment solution.
Figure 1D:
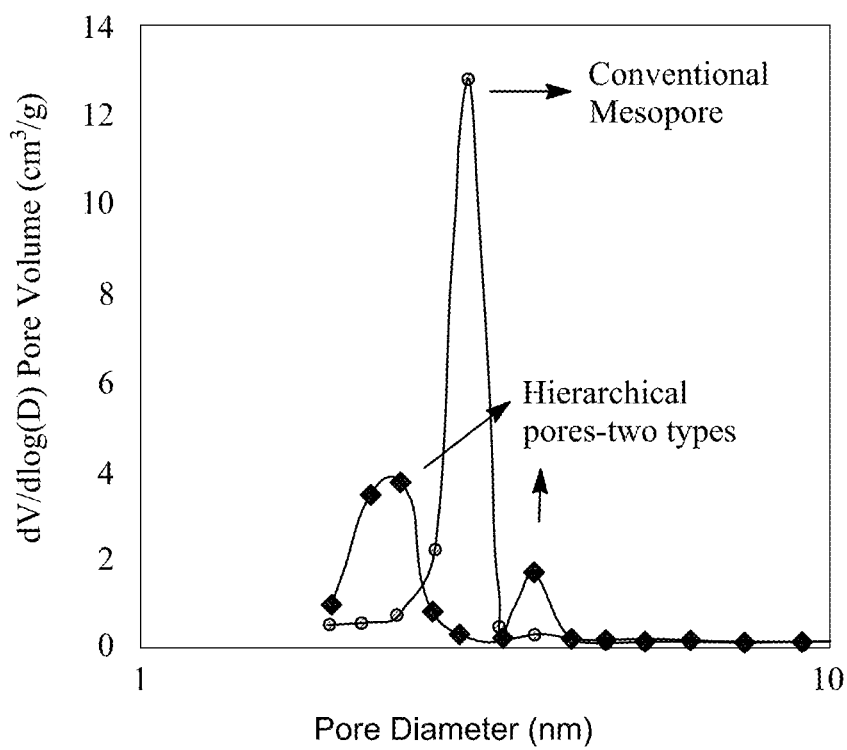
FIG. 1D shows pore size distribution of mesosilicalite prepared using 0.7M NaOH treatment solution.

Characterization of Cisplatin Nanocarriers:

Hierarchical mesosilicalite was synthesized using silicalite precursors through top-down methodology. In this technique, a full grown silicalite containing micropores were treated with 0.7M NaOH solution that breaks it down to nanosized silicalite seed solution. The presence of mesotemplate CTAB at hydrothermal condition at 100° C. allows the formation of meso-structure of hexagonal SiMCM-41 containing hierarchical pores of nanocomposite. The XRD patterns of the mesoporous silica conventional SiMCM-41, the microporous zeolite silicalite, the meso/micro nanocomposite hierarchical mesosilicalite, and cisplatin loaded mesosilicalite nano-formulation are shown in FIGS. 1A and 1B. Conventional SiMCM-41 showed three well resolved peaks observed at low angle region (2-5θ) indexed to (100), (110), and (200) reflections assigned to hexagonal symmetry [Kresge et al. "Ordered mesoporous molecular sieves synthesized by a liquid-crystal template mechanism" Nature 1992, 359, 710-7—incorporated herein by reference]. Silicalite displays a characteristics high angle diffraction pattern between 8-10 θ and 20-40 θ indicating the presence of pure silicalite phase with structure similar to that of ZSM-5 [Yang et al. "Fabrication of SiO2@silicalite-1 and its use as a catalyst support", RSC Adv. 2017, 7, 12224—incorporated herein by reference]. In case of mesosilicalite, the diffraction pattern shows interrelated meso and microphases composed of both hexagonal SiMCM-41 (2 θ angle (2-5θ)) and silicalite (8-60θ) indicating nanocomposite formation. Compared to conventional SiMCM-41 (d100=4.45 nm), the d-spacing of mesosilicalite decreased (d100=3.82 nm) suggesting the interrelated framework rearrangement due to the presence of zeolitic phase in MCM-41 structure. Overall, the synthesized silicalite based nanocomposite material contained microphase of silicalite-like aluminum rich ZSM-5/MCM-41 composite [Boukoussa et al. Key factor affecting the structural and textural properties of ZSM-5/MCM-41 composite, J. Phys. Chem. Solids, 2015, 78, 78-83—incorporated herein by reference]. FIG. 1C and 1D) shows the adsorption isotherms for conventional SiMCM-41 and mesosilicalite. Table 1 summarizes specific surface area, pore diameter (PD), and the total specific pore volume (TPV) of SiMCM-41, silicalite and mesosilicalite. Conventional SiMCM-41 showed a typical adsorption-desorption hysteresis characteristic of ordered mesopores of MCM-41. The exhibition of type-IV isotherm and typical steep inflection capillary condensation phenomena at p/p0=0.3–0.4 indicates the presence of high surface texture with unidimensional type of pores. The surface area of SiMCM-41 was 1119 m2g-1 with pore diameter centered around 2.7 nm (Table 1). The parent silicalite showed typical isotherm pattern characteristics of micropores. Alkaline treatment of microporous silicalite (0.7M NaOH) shows considerable mesoporosity formation with remodulation of isotherm hysteresis (type IV to intermediate between type I and IV) indicating the presence of hierarchical pores (FIG. 1C). Unlike conventional SiMCM-41, a less sharp capillary condensation is observed, which indicates broader type hierarchical pores in the nanocomposite. In addition, formation of H4-type hysteresis loop at relative pressure $p/p_o>0.45$ indicates hierarchical pores due to ingrained matrix between mesopores and micropores [Rutkowska et al. "Hierarchically structured ZSM-5 obtained by optimized mesotemplate-free method as active catalyst for methanol to DME conversion" Catal. Sci. Technol. 2016, 6, 4849-4862—incorporated herein by reference]. The textural property presented in Table 1 shows that the mesoporous surface area decreases to 830 m2g-1, and the pore size distribution shows the presence of dual type of pores centered at about 2.4 nm and 3.8 nm, respectively (FIG. 1D).

Figure 2A:
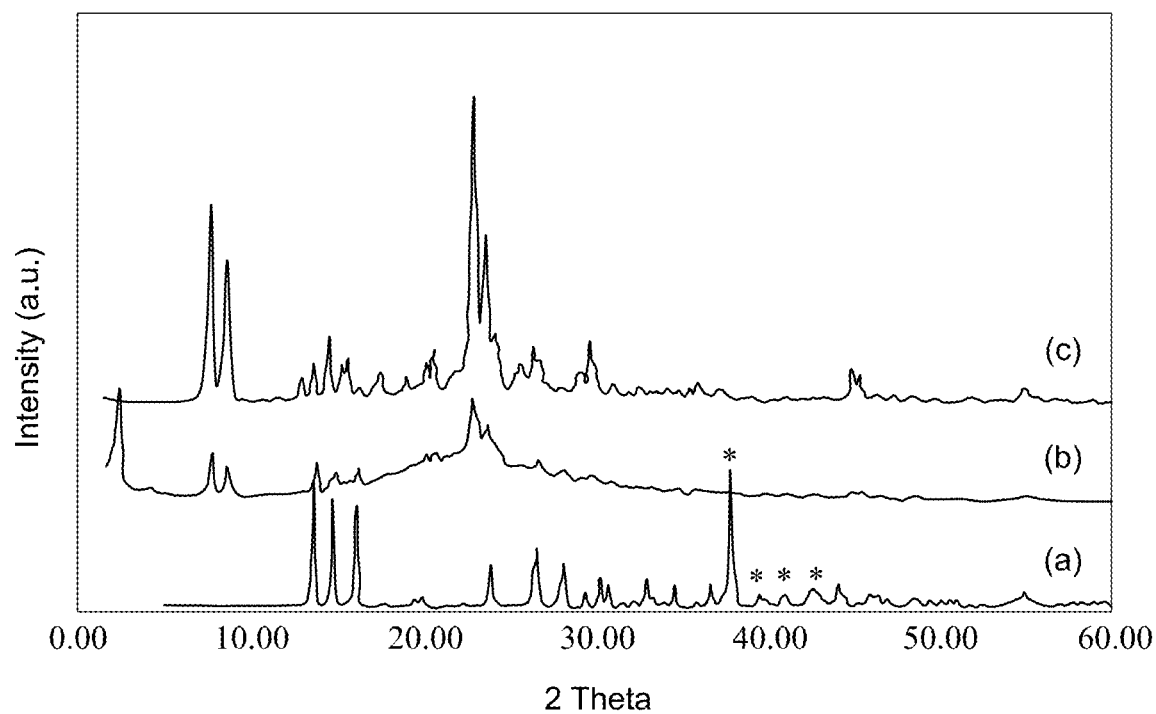
FIG. 2A shows XRD diffraction spectra of (a) cisplatin, (b) IAUM-56, and (c) precursor silicalite.
Figure 2B:
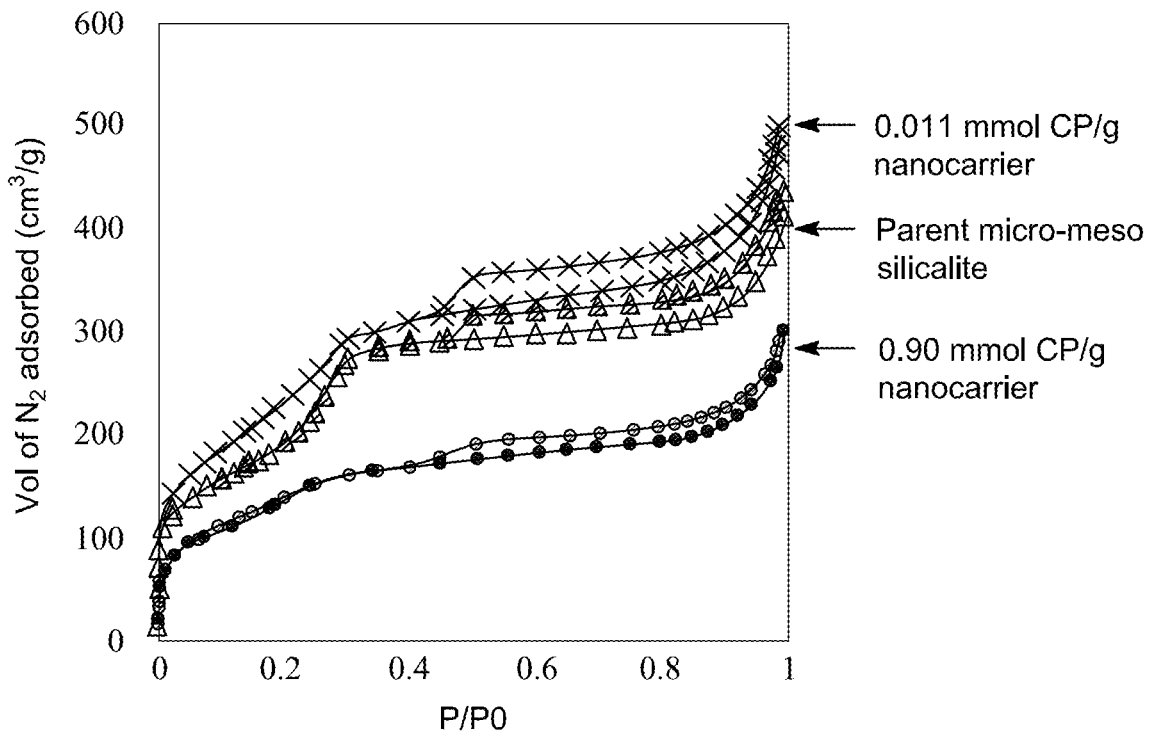
FIG. 2B shows nitrogen adsorption isotherm effect over cisplatin loaded hierarchical mesosilicalite compared with conventional mesoporous SiMCM-41.
Figure 2C:
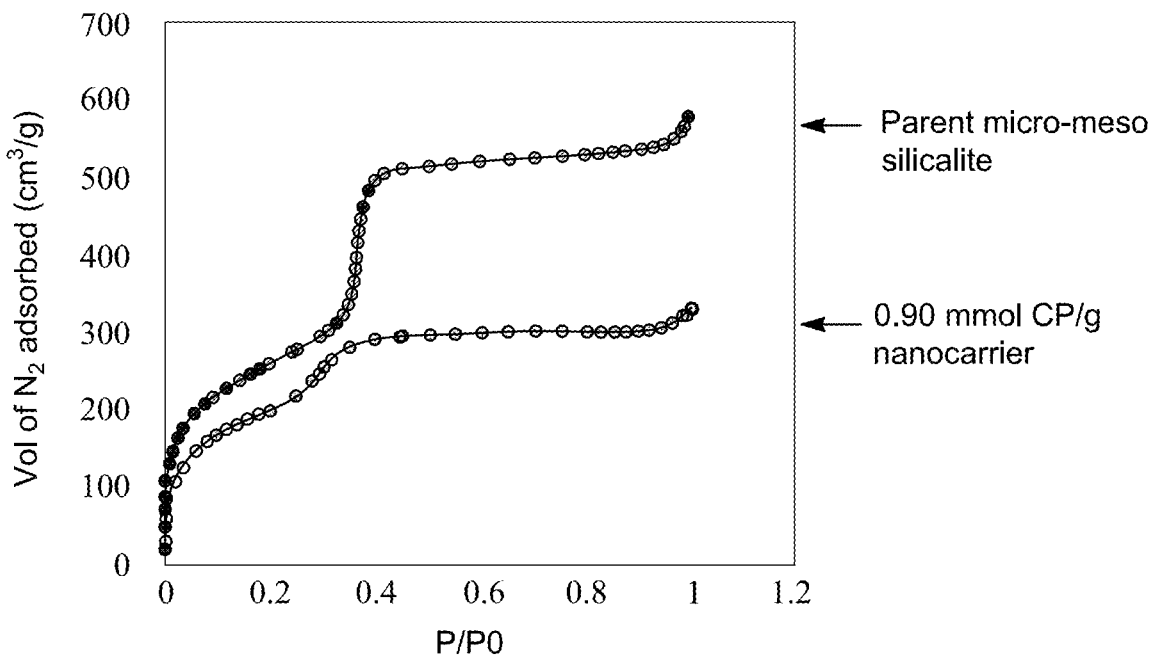
FIG. 2C shows nitrogen adsorption isotherm effect over conventional mesoporous SiMCM-41.
Figure 2D:
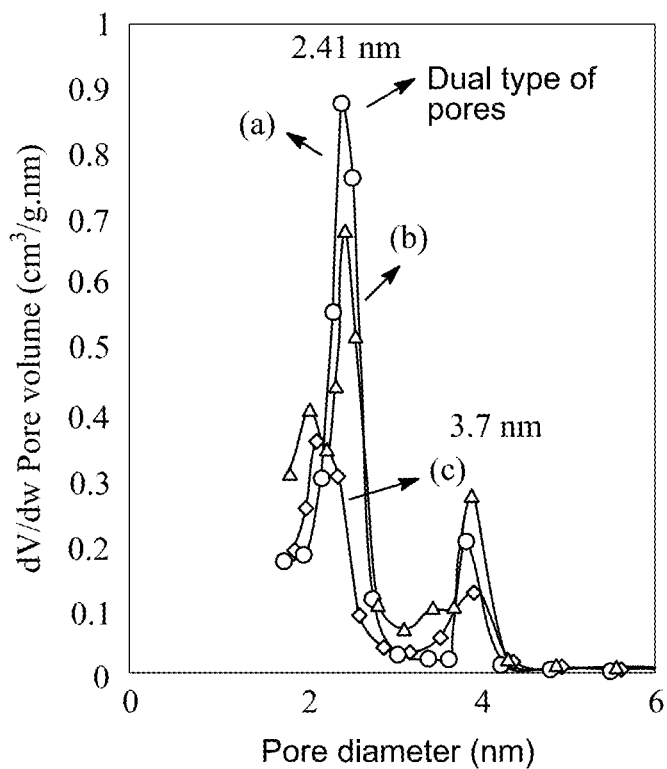
FIG. 2D shows pores size distribution of cisplatin loaded hierarchical mesosilicalite.
Figure 2E:
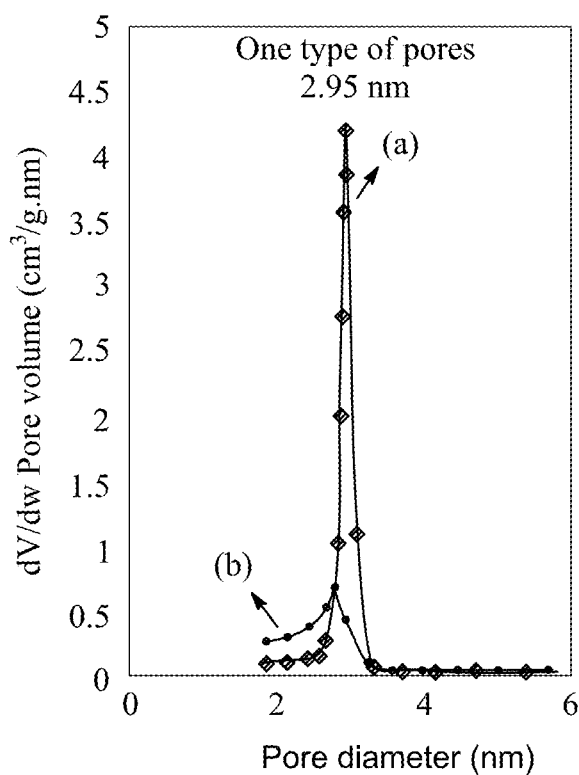
FIG. 2E shows pore size distribution of conventional mesoporous SiMCM-41.

In case of IAUM-56, similar diffractions of hexagonal mesophase and silicalit microphase to that of the parent mesosilicalite were observed. With cisplatin loading, further decrease in the d-spacing to 3.57 nm was observed. The diffraction pattern of silicalite was found to be overlapping with cisplatin diffraction peaks. However, complete disappearance of the characteristic cisplatin peaks at 2θ 37, 39, 40 and 42 showed a clear transformation of crystalline form into nanoform over mesosilicalite deposition (FIG. 2A(a-c)). FIGS. 2B and 2C show the textural parameters of IAUM-56 and conventional SiMCM-41 after cisplatin loading with 0.011 and 0.9 mmol of cisplatin per gram of nanocarrier in NSS. Similar to the parent mesosilicalite (see FIGS. 1C and 1D), IAUM-56 displays intermediate isotherm indicating the preservation of the micro- and mesopores textural characteristics after cisplatin loading with 0.011 mmol of cisplatin per gram of nanocarrier, (see FIG. 2B). The surface area of IAUM-56 remains high at about 948 m2/g, with pore volume of 0.77 cc/g. The presence of dual type of pores in IAUM-56 is observed at pore diameters centered at about 2.4 nm and 3.9 nm (see Table 1 and FIG. 2D). In case of conventional SiMCM-41, a typical isotherm with only one type of pores is observed centered at 2.7 nm (see FIGS. 2C and 2E). The presence of mesosilicalite in saline solution tends to enhance the textural characteristics of surface area of IAUM-56. Significantly, increasing cisplatin loading to 0.9 mmol of cisplatin per gram of nanocarrier showed only 10% reduction in the surface area and 16% reduction in pore volume indicating that the carrier may be loaded with even larger amount of cisplatin loading (Table 1).

TABLE 1

Textural characteristics of conventional SiMCM-41, silicalite and cisplatin/mesosilicalite.

| Sample | Composite | Cisplatin content (mmolCP/g support) | BET Surface area ($m^2/g$) | BJH adsorption Cumulative Surface area ($m^2/g$) | Pore volume (mL/g) | Pore diameter (nm) |
|---|---|---|---|---|---|---|
| Silicalite | Microporous | — | 308 | 117 | 0.20 | 2.6 |
| IAUM-27 | Micro/meso (hierarchial) | — | 830 | 861 | 0.63 | 2.4 3.8 |
| IAUM-56 | Micro/meso (hierarchial) | 0.011 | 948 | 938 | 0.77 | 2.4 3.9 |
| IAUM-57 | Micro/meso (hierarchial) | 0.90 | 742 | 738 | 0.53 | 2.3 3.8 |
| MCM-41 | mesoporous | — | 942 | 1200 | 0.87 | 2.9 |
| IAUM-55 | mesoporous | 0.90 | 1119 | 1192 | 0.8 | 2.7 |

Figure 3:
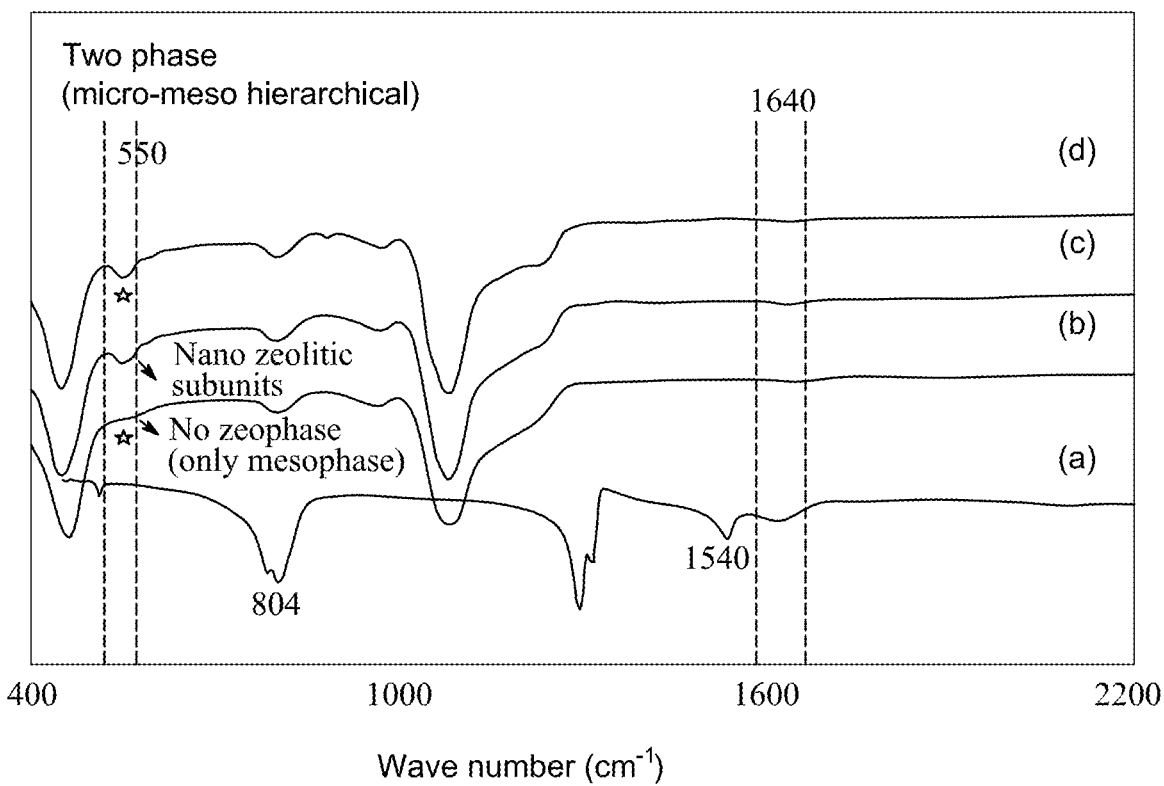
FIG. 3 shows FTIR spectra of (a) cisplatin, (b) cisplatin/SiMCM-41 (IAUM-55), (c) cisplatin/mesosilicalite (IAUM-57) and (d) cisplatin/mesosilicalite (IAUM-56).

Infrared spectroscopy was used for probing the atomic ordering of mesozeolitic type materials. FIG. 3 shows the FTIR spectra: (a) cisplatin, (b) cisplatin/SiMCM-41 (IAUM-55), (c) cisplatin/mesosilicalite (IAUM-57) and (d) cisplatin/mesosilicalite (IAUM-56), respectively. In case of SiMCM-41 and hierarchical mesosilicalite, a distinct difference was observed with respect to hierarchical character with presence of two phase of micro/meso nanocomposite. The FTIR of the mesosilicalite showed the presence of five membered rings characteristics of nanozeolitic subunits at about 550 cm-1 similar to that of pure ZSM-5. In the case of acidic type zeolite ZSM-5 transformation into ZSM-5/MCM-41 composite and ZSM-5-SAPO-5/MCM-41 composite, similar five ring subunits are observed and shown to prove the incorporation of zeolitic subunits into the framework walls of the mesostructured through ion-pairing [Liu et al. "Aluminosilicate Mesostructures Assembled from Zeolite ZSM-5 and Zeolite Beta Seeds, Angew. Chem. Int. Ed. 2001, 40, 1255]. The intensity of the band of mesosilicalite indicates the large extent of the zeolite characteristics throughout the silica walls framework during nanocomposite formation which is distinct from merely a physical mixture of SiMCM-41 and silicalite. It has been further explained that alkaline treatment in the presence of ionic template such as CTAB favors electrostatic interactions between nanoseeds of zeolite and positively charged template and leads to the formation of zeolite stabilized hexagonal mesostructured [Huang et al. "Investigation of Synthesizing MCM-41/ZSM-5 Composites", J. Phys. Chem. B, 2000, 104, 2817-2823; Areana et al. "Effect of amine and carboxyl functionalization of sub-micrometric MCM-41 spheres on controlled release of cisplatin", Ceramics International 2013, 39, 7407-7414—incorporated herein by reference]. In case of SiMCM-41, there was no FTIR absorption at about 550 $cm^{-1}$ indicating the presence of pure amorphous characteristics. A broad peak of 1637 $cm^{-1}$ shows the characteristic peaks of cisplatin. IAUM-55, IAUM-56 and IAUM-57 display the presence of bending vibration at 1640 cm-1 indicates the functionalization of cisplatin and reaction between silica and Platinum(II) complex.

Figure 4:
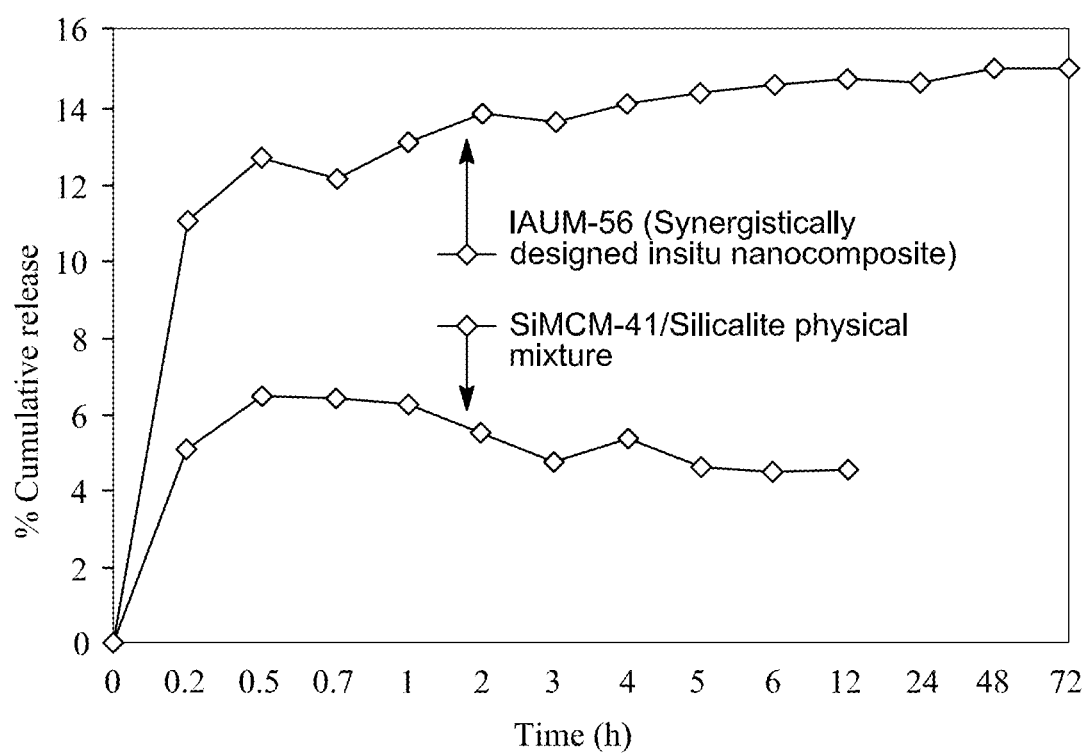
FIG. 4 shows a cisplatin release profile from IAUM-56 and physically mixed SiMCM 41/Silicalite mixture at pH 5.

The drug release profile of IAUM-56 is subjected to simulated tumor acidic condition at pH 5.0 and 37° C. for 72 h. The study shows that a steady drug release is observed for 72 h with slower kinetics (see FIG. 4). At pH 5.0, the release of cisplatin from the carrier is controlled by the electrostatic interactions between cisplatin/mesosilicalite nanoformulation and the acidic medium. In case of the physically mixed sample of SiMCM-41/Silicalite, the lower drug release effect with less than 7% shows the importance of synergism between meso and microphase of SiMCM-41 and Silicalite of IAUM-56 leading to the formation of hierarchical pores through the in-situ preparation.

EXAMPLE 5

In-vitro anticancer activity study: Anticancer activity of hierarchical mesosilicalite of IAUM-27 and 0.011 mmol cisplatin/gram of mesosilicalite (IAUM-56) are compared on cervical cancer cell line HeLa and breast cancer cell line MCF7, purchased from HyClone, GE Healthcare, Chicago, USA. The cells are grown in RPMI medium with 10% fetal calf serum and 1×penicillin/streptomycin solution purchased from Thermo Fisher, Waltham, USA. The cells were seeded at the rate of $1\times10^4$ cells/well of a 96 well plate. None cancerous normal dermal fibroblast primary cells maintained in house are used as a control cell line. After 24 hours of culture at 37° C., 95% relative humidity and 5% $CO_2$ levels, cells are treated with varied concentration of test drugs hierarchical mesosilicalite (IAUM-27) and IAUM-56 along with the solvent in which the drugs are solubilized. Upon further culture for another 48 hours, the cells are subjected to end point cell survival assay using MTT (3-(4, 5-dimethylthiazol-2-yl)-2,5-diphenyltetrazolium bromide) dye reduction test.

MTT Assay: To each of the drug treated and control 96 culture wells, 20 µl of 10 mg/ml MTT was added and incubated for up to 24 hours under the same culturing conditions described above. The wells were washed off the unbound dye using ample amounts of PBS (Phosphate buffered saline: Thermo Fisher, Waltham, USA). The formazan dye formed was solubilized by adding 150 µl of 0.1% NP40 in isopropanol (MTT solvent) and shaken on a plate shaker for 15 mins. The optical density (OD) of the solubilized dye was read at 590 nm using a multiplate reader (Tecan Infinite® 200 PRO, Tecan Trading AG, Switzerland). The OD was compared and calculated against control and expressed as percentage of cell survival.

Figure 5A:
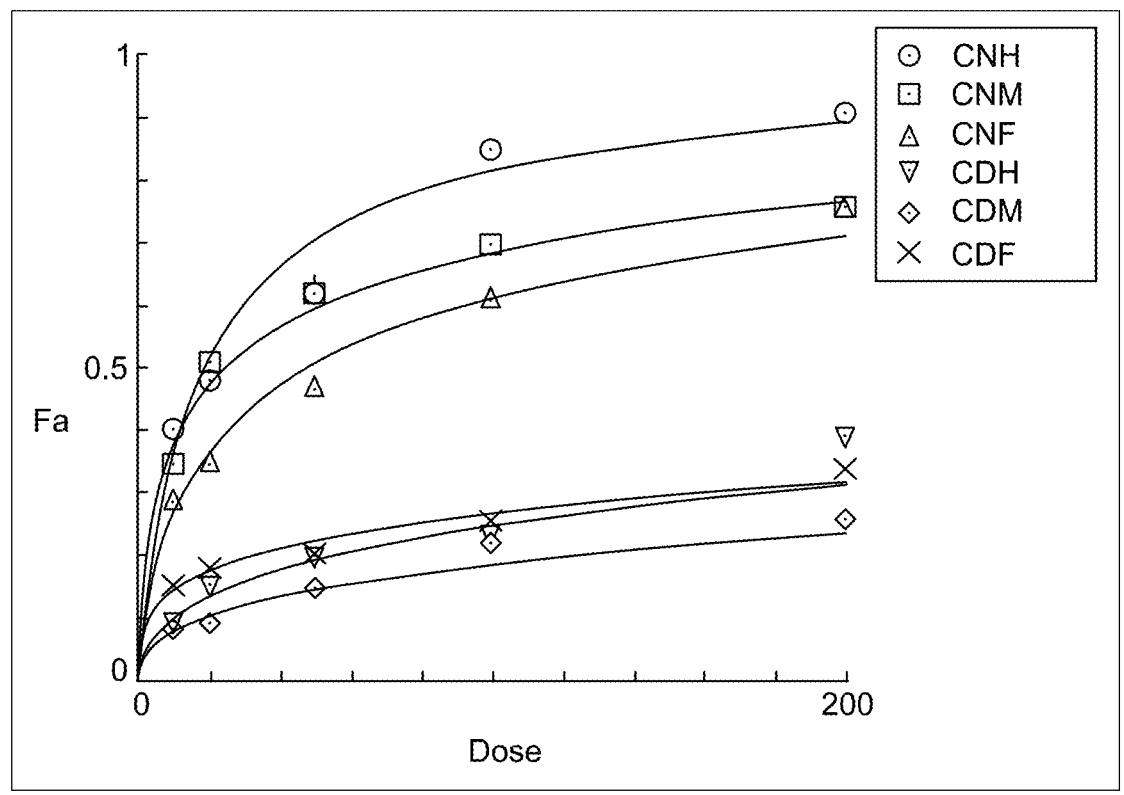
FIG. 5A shows a plot of the fraction of cells affected (Fa) vs drug dose in μM when cisplatin was prepared either in DMSO or in NSS (0.9% NaCl) [CNH: cisplatin in NSS on HeLa cells; CNM: cisplatin in NSS on MCF7 cells; CNF: cisplatin in NSS on Fibroblasts; CDH: cisplatin in DMSO on HeLa cells; CDM: cisplatin in DMSO on MCF7 cells; CDF: cisplatin in DMSO on Fibroblasts].
Figure 5B:
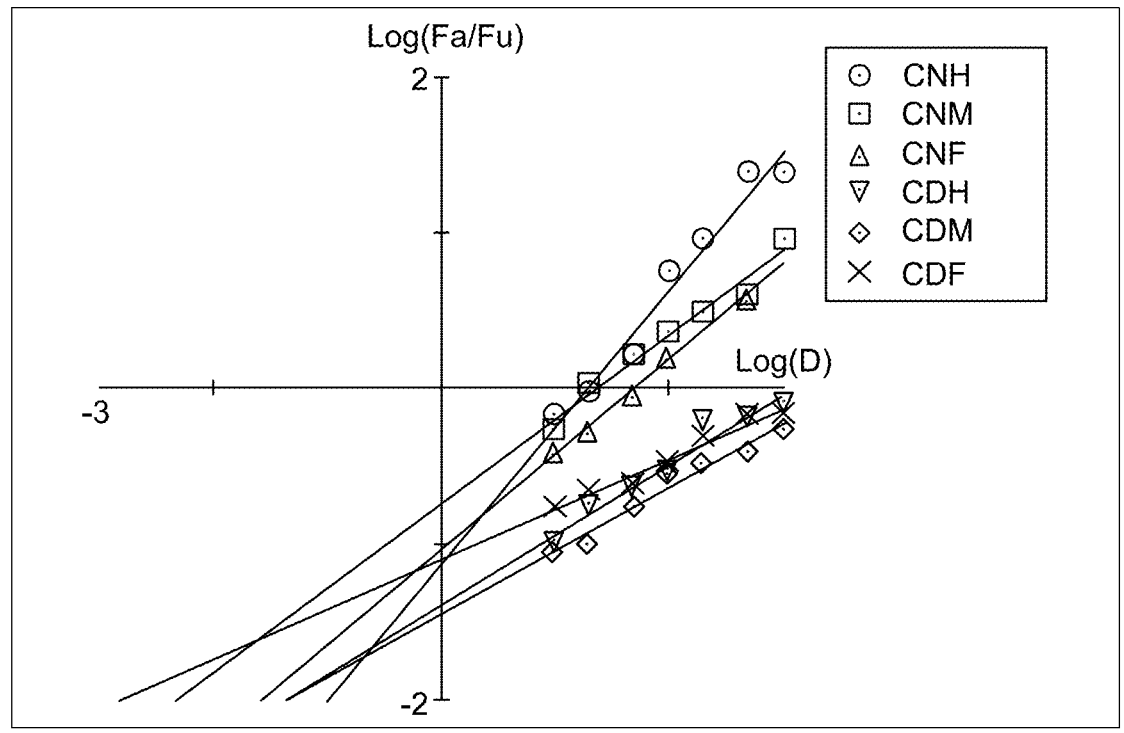
FIG. 5B shows plots of log Fa/Fu vs log drug dose when cisplatin was prepared either in DMSO or in NSS (0.9% NaCl) [CNH: cisplatin in NSS on HeLa cells; CNM: cisplatin in NSS on MCF7 cells; CNF: cisplatin in NSS on Fibroblasts; CDH: cisplatin in DMSO on HeLa cells; CDM: cisplatin in DMSO on MCF7 cells; CDF: cisplatin in DMSO on Fibroblasts].

In vitro MTT assay is an essential tool to study the safety of anticancer drugs and to determine the effective dose for new drug therapy. A good drug candidate has to be effective in killing the cancer cells, while exerting negligible toxicity on normal cells. In order to evaluate this condition, MTT assay is carried out with mesosilicalite and cisplatin/mesosilicalite nanocomposite. FIG. 5A shows a plot of the fraction of the cell affected (Fa) vs. drug dose in µM, wherein the drug in DMSO or in normal saline solution (NSS, 0.9% NaCl), and the LC50's are calculated from the plots of log Fa/Fu vs log D (see FIG. 5B). Table 2 shows the LC50 values for cisplatin dissolved in DMSO and NSS and loaded on the nanocarrier treated Hela, MCF-7 and normal Fibroblast cells.

TABLE 2

LC50 values for Cisplatin dissolved either in DMSO or NSS on cancer and normal cells

| Drug-Vehicle-Cells | LC50$^a$ (µM) | Std. dev. | R |
|---|---|---|---|
| CNH | 18.6882 | 1.8456 | 0.98304 |
| CNM | 24.1290 | 2.2258 | 0.98509 |
| CNF | 48.7722 | 4.6571 | 0.98846 |
| CDH | 1255.23 | 125.356 | 0.97352 |
| CDM | 3817.55 | 145.365 | 0.98112 |
| CDF | 2422.35 | 139.478 | 0.98561 |

LC50 values with different superscripts vary significantly ($P < 0.05$).
CNH: Cisplatin in NSS on HeLa cells,
CNM: Cisplatin in NSS on MCF7 cells,
CNF: Cisplatin NSS on Fibroblasts,
CDH: Cisplatin in DMSO on HeLa cells,
CDM: Cisplatin in DMSO on MCF7 cells,
CDF: Cisplatin in DMSO on Fibroblasts.

FIG. 5 and Table 2 conclusively shows that NSS has showed better solubility and stability for the cisplatin than DMSO as seen from the dose response curve and LC50 value (Table 2).

Figure 6A:
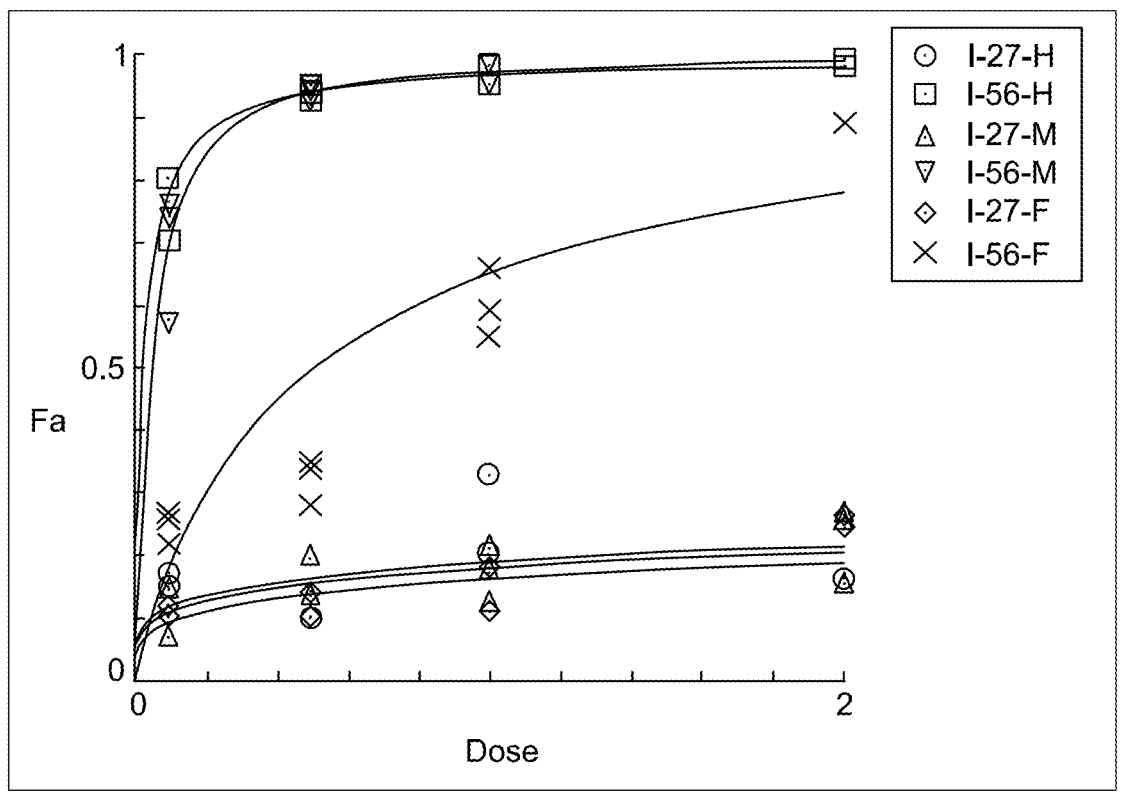
FIG. 6A shows dose a plot of the fraction of cells affected (Fa) vs drug dose in mg/ml upon treatment of IAUM-27 and IAUM-56 on HeLa, MCF7 and normal fibroblast cells.
Figure 6B:
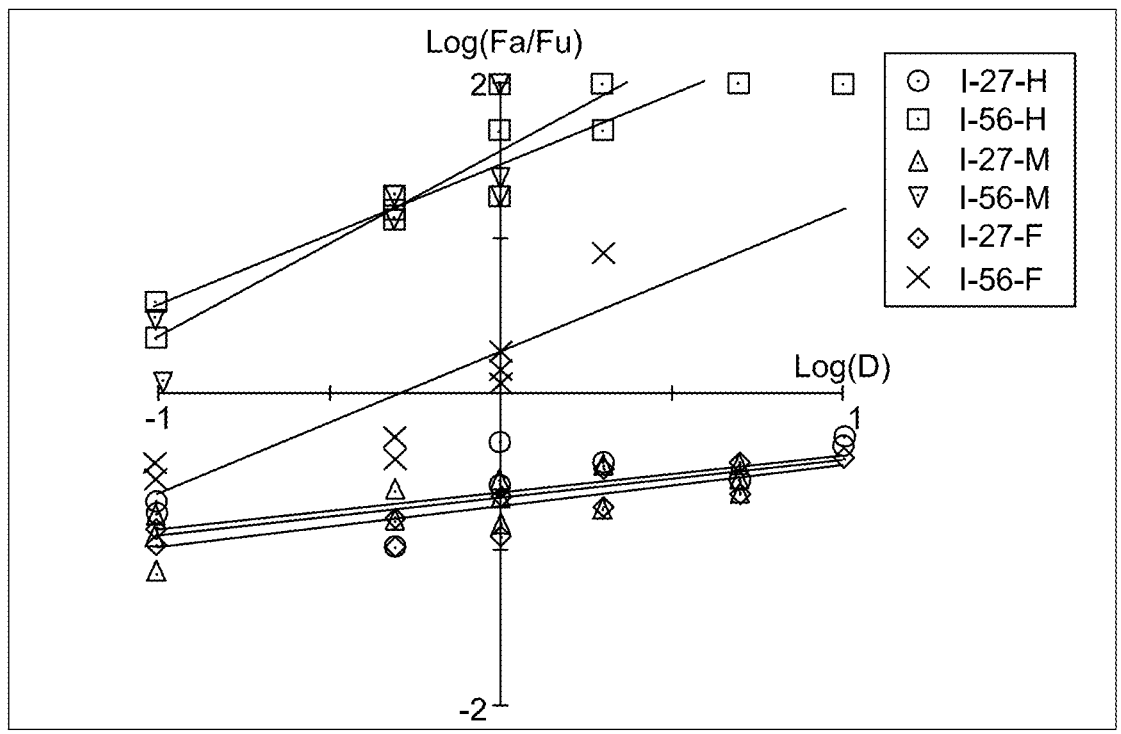
FIG. 6B shows a plot of log Fa vs log drug dose in mg/ml upon treatment of IAUM-27 and IAUM-56 on HeLa, MCF7 and normal fibroblast cell.
Figure 7A:
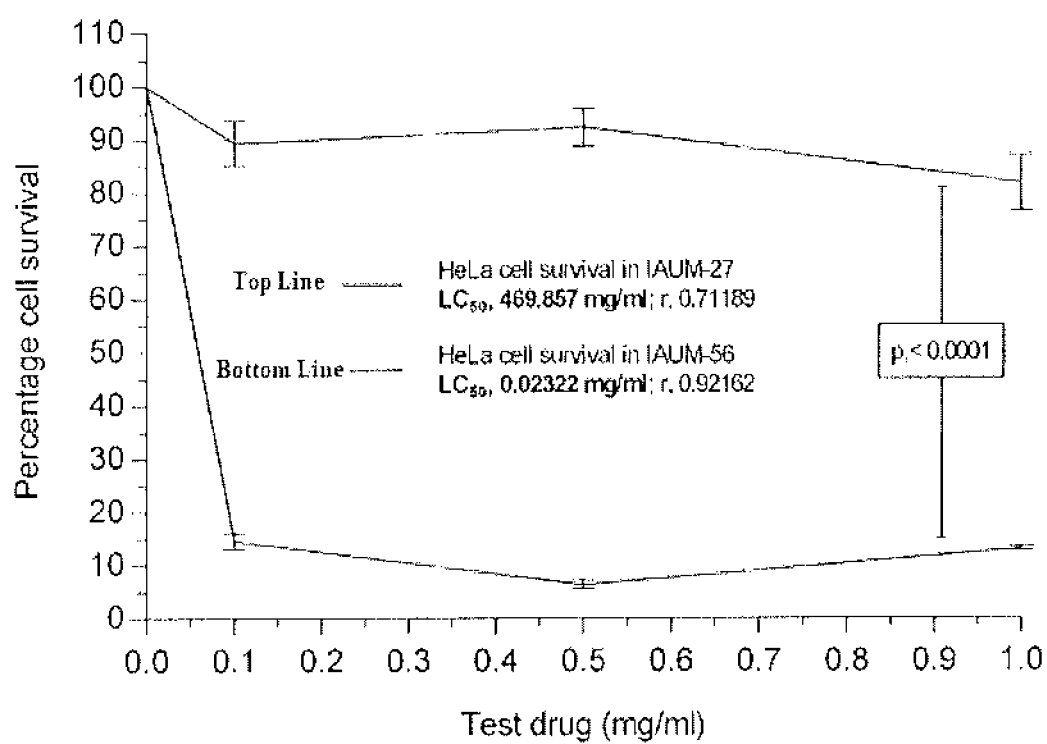
FIG. 7A shows cytotoxic effect of cisplatin loaded mesosilicalite (IAUM-56) on HeLa cells.
Figure 7B:
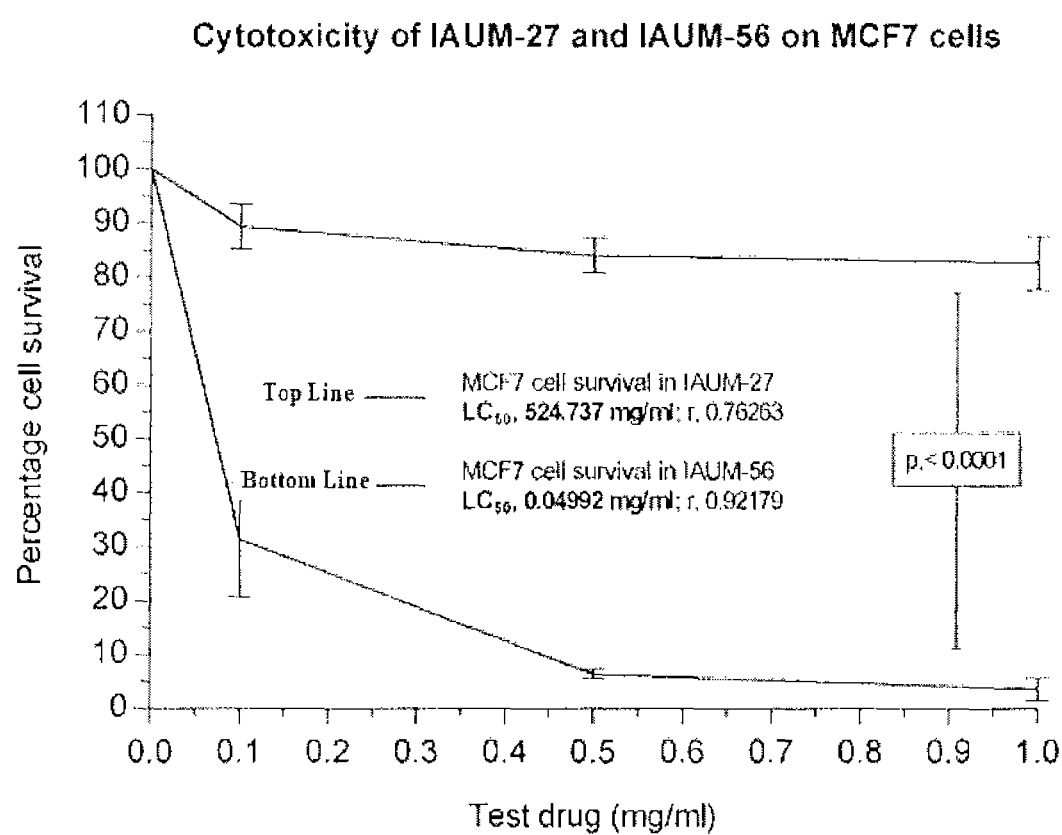
FIG. 7B shows cytotoxic effect of cisplatin loaded mesosilicalite (IAUM-56) on MCF7 cells.
Figure 7C:
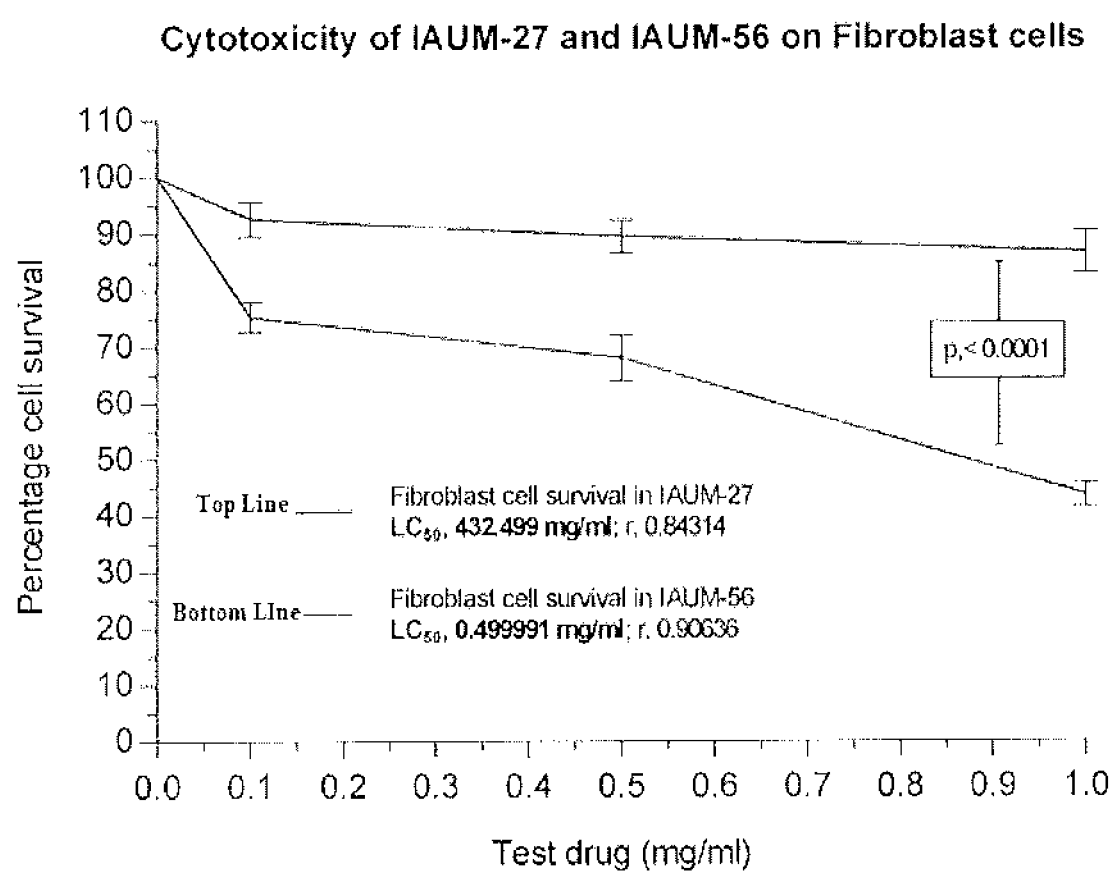
FIG. 7C shows cytotoxic effect of cisplatin loaded mesosilicalite (IAUM-56) on normal fibroblast cells.
Figure 7D:
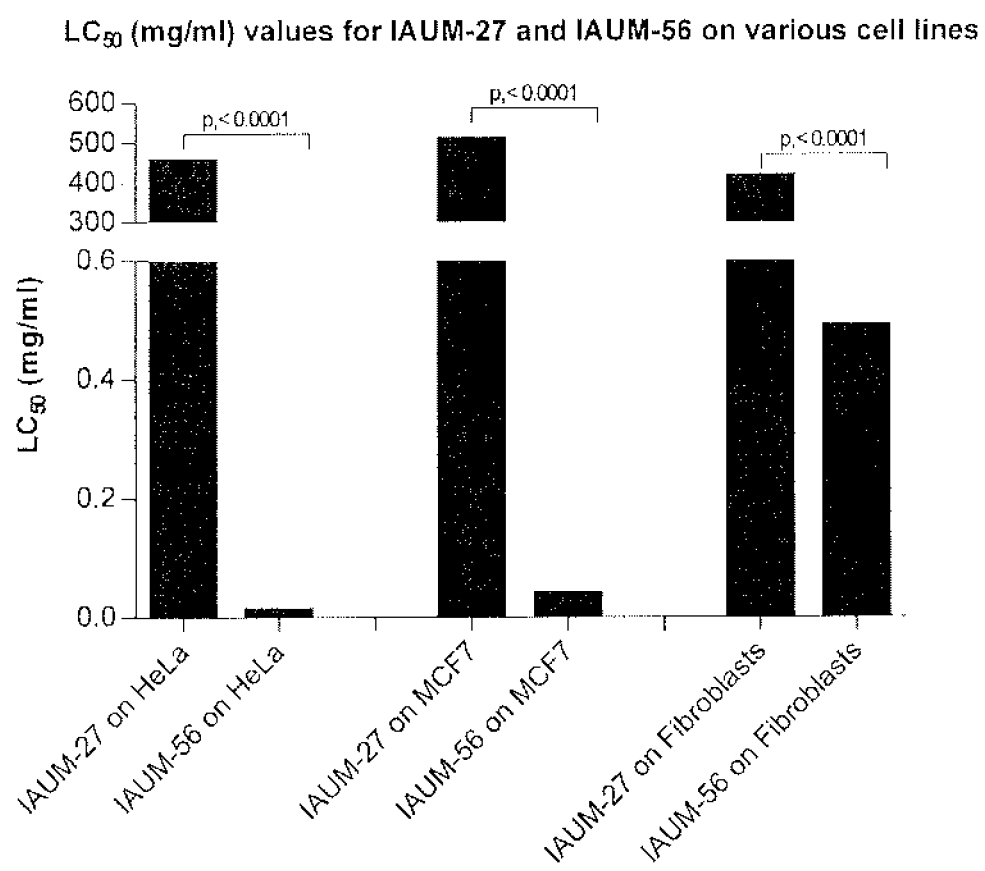
FIG. 7D shows a comparison of the cytotoxic effect of IAUM-27 and IAUM-56 on HeLa cells, CMF7 cells, and fibroblast cells as measured by $LC_{50}$.

The dose effect curve FIG. 6A is a plot of the fraction of cells affected (Fa) vs drug dose (mg/ml) upon treatment of mesosilicalite alone (IAUM-27) and cisplatin/mesosilicalite (IAUM-56) on HeLa, MCF7 and normal fibroblast cells. LD50s values are calculated from plots of log Fa/Fu vs log D shown in FIG. 6B and listed in Table 3. Median-effect plot (B). Alphabet succeeding drug-H (I-27-H and I-56-H), HeLa cells; M (I-27-M and I-56-M), MCF7 cells; F, Fibroblast cells (FIG. 6). Spherical MCM-41 synthesized through Stober's route functionalized with silanes (3-aminopropyl triethoxysilane and 3-propanonitrile triethoxysilane) and carboxyl group are shown to have sustained release of cisplatin and improvement of cisplatin loading than MCM-41 [Areana et al. Effect of amine and carboxyl functionalization of sub-micrometric MCM-41 spheres on controlled release of cisplatin, *Ceramics International* 2013, 39, 7407-7414—incorporated herein by reference]. MCM-41 showed a lower cisplatin loading capacity with only 9 mg cisplatin per gram in aqueous medium. Marginal improvement of less than 2 fold to 15 mg/g is observed with carboxyl functionalization compared to pure MCM-41 loading In contrast, the silane functionalized MCM-41 showed six-fold increase of cisplatin adsorption (61 mg/g). The cytotoxic effect of cisplatin loaded mesosilicalite (IAUM-56) against HeLa cells (A), MCF7 cells (B), and normal fibroblast cells (C) are shown in FIG. 7. IAUM-56 was found to be highly cytotoxic against HeLa cells (A) with an LC50 of 0.02 mg/ml, MCF7 cells (B) with an LC50 of 0.05 mg/ml and less toxic to normal fibroblast cells (C) with an LC50 of approximately 10 times higher of 0.5 mg/ml. Drug loaded mesosilicalite (IAUM-56) shows targeted cytotoxicity against cancer cells while affecting normal cells at much lesser rate (FIG. 7). This study clearly elucidates that in-house designed nanomaterial did not show lethal activity/toxic effect on normal fibroblast cells. At the same time, IAUM-56 nanoformulation involving cisplatin/mesosilicalite nanocomposite with less dose of cisplatin shows exemplary inhibitory activity on MCF7 cells and HeLa cells indicating highly efficient synergistic nano-formulation. FIGS. 5A dose effect curve and FIG. 5B median-effect plot depicts the fraction of cells affected (Fa) vs drug dose (µM) when cisplatin was prepared either in DMSO or in NSS (0.9% NaCl) (CNH: cisplatin in NSS on HeLa cells, CNM: cisplatin in NSS on MCF7 cells, CNF: cisplatin in NSS on Fibroblasts, CDH: cisplatin in DMSO on HeLa cells; CDM: cisplatin in DMSO on MCF7 cells, CDF: cisplatin in DMSO on Fibroblasts), respectively.

TABLE 3

LC50 values for mesosilicalite (IAUM-27) and Cisplatin loaded mesosilicalite (IAUM-56) nano carriers on cancer and normal cell

| Drug-Cells | $^a$LC50 (mg/ml) | Std dev. | r |
|---|---|---|---|
| IAUM27-HeLa | 469.857 | 15.654 | 0.71189 |
| IAUM56-HeLa | 0.0232 | 0.0176 | 0.92162 |
| IAUM27-MCF7 | 524.737 | 18.954 | 0.76263 |
| IAUM56-MCF7 | 0.04992 | 0.0365 | 0.92179 |
| IAUM27-Fibroblast | 432.499 | 14.562 | 0.84314 |
| IAUM56-Fibroblasts | 0.49991 | 0.1587 | 0.90636 |

$^a$LC50 values vary significantly ($P < 0.05$)

Figures 8A, 8B, 8C, 8D, 8E, 8F:
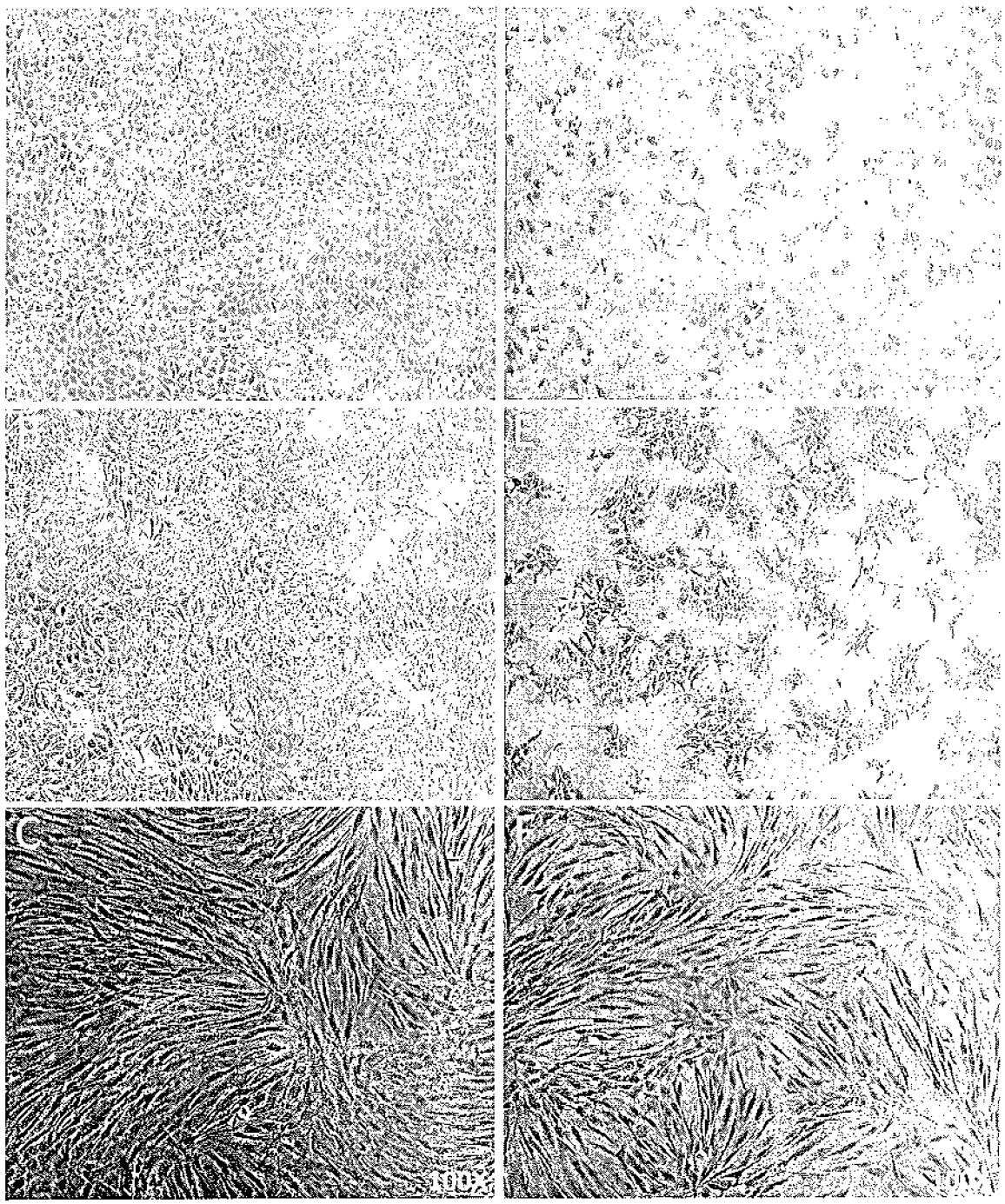
FIG. 8A shows a microphotograph of control culture of HeLa cervical cancer cells treated with hierarchical mesosilicalite without cisplatin (IAUM-27) as described in MTT assay.
FIG. 8B shows a microphotograph of control culture of MCF7 breast cancer cells treated with hierarchical mesosilicalite without cisplatin (IAUM-27) as described in MTT assay.
FIG. 8C shows a microphotograph of control culture of fibroblast HeLa cells treated with hierarchical mesosilicalite without cisplatin (IAUM-27) as described in MTT assay.
FIG. 8D shows a microphotograph of culture of HeLa cervical cancer cells treated with hierarchical mesosilicalite comprising cisplatin (IAUM-56) as described in MTT assay.
FIG. 8E shows a microphotograph of culture of MCF7 breast cancer cells treated with hierarchical mesosilicalite comprising cisplatin (IAUM-56) as described in MTT assay.
FIG. 8F shows a microphotograph of control culture of fibroblast HeLa cells treated with hierarchical mesosilicalite comprising cisplatin (IAUM-56) as described in MTT assay.
Figure 9A:
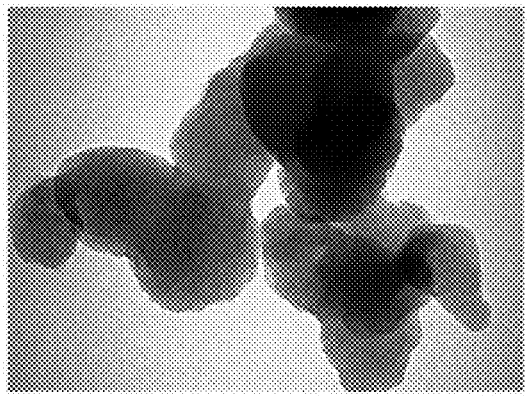
FIG. 9A shows transmission electron microscope images of conventional SiMCM-41.
Figure 9B:
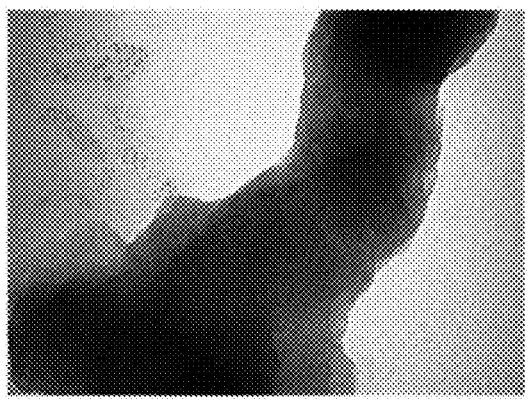
FIG. 9B shows transmission electron microscope images cisplatin/SiMCM-41 in DMSO (IAUM-35).
Figure 9C:
FIG. 9C shows transmission electron microscope images of cisplatin/SiMCM-41 in NSS (IAUM-55).
Figure 9D:
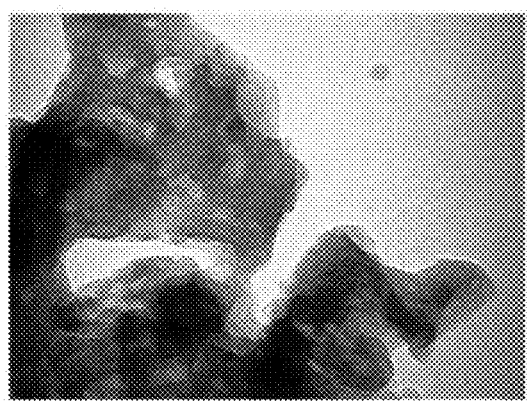
FIG. 9D shows transmission electron microscope images mesosilicalite.
Figure 9E:
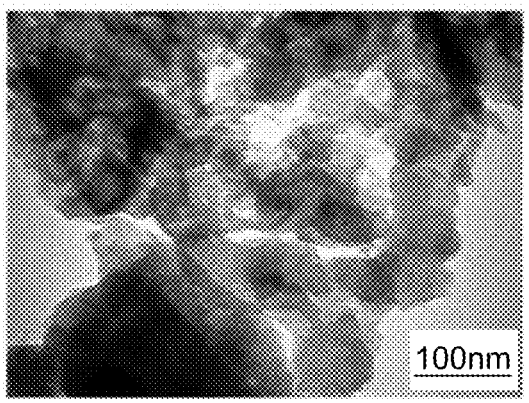
FIG. 9E shows transmission electron microscope images of cisplatin/mesosilicalite in DMSO (IAUM-34).
Figure 9F:
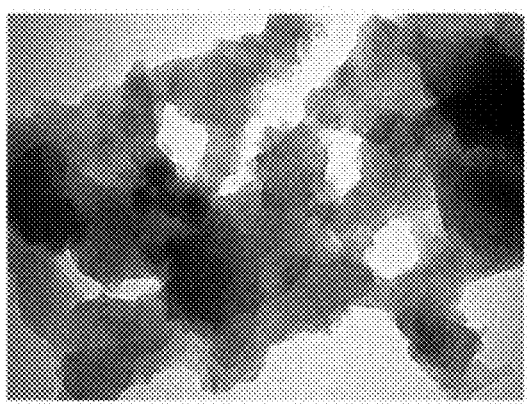
FIG. 9F shows transmission electron microscope images of cisplatin/mesosilicalite in NSS (IAUM-56).
Figure 9G:
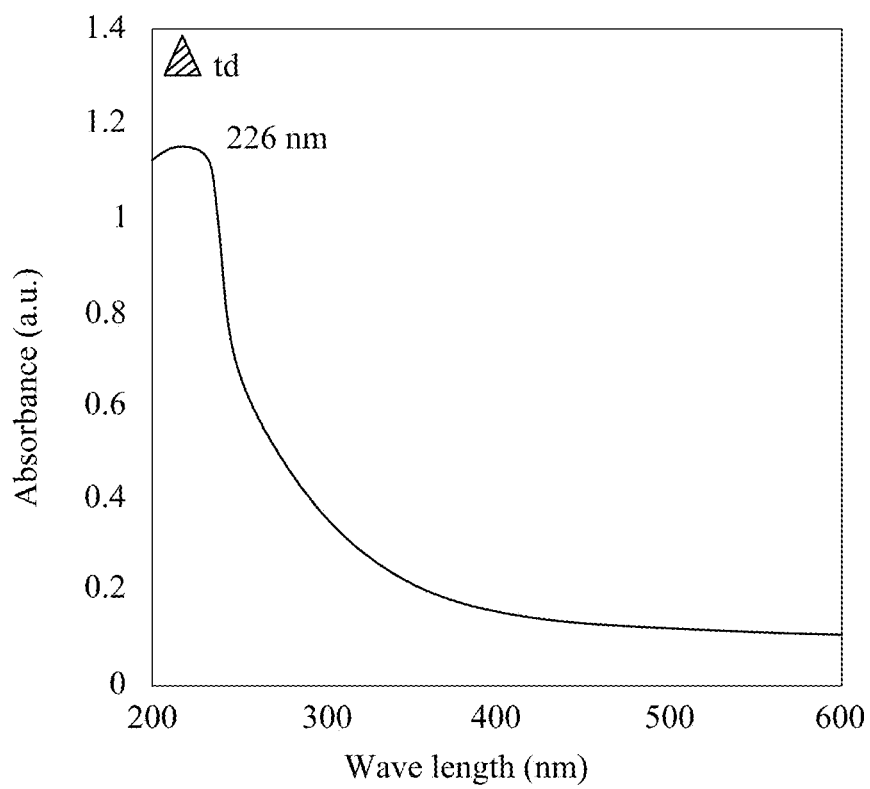
FIG. 9G shows Drs-UV spectra of IAUM-34 prepared in DMSO.
Figure 9H:
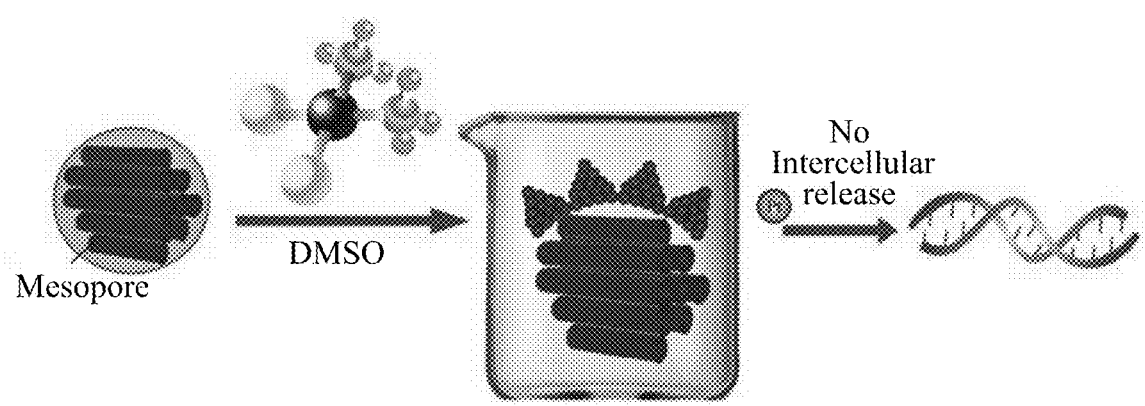
FIG. 9H shows schematic presentation of IAUM-34 prepared in DMSO.
Figure 9I:
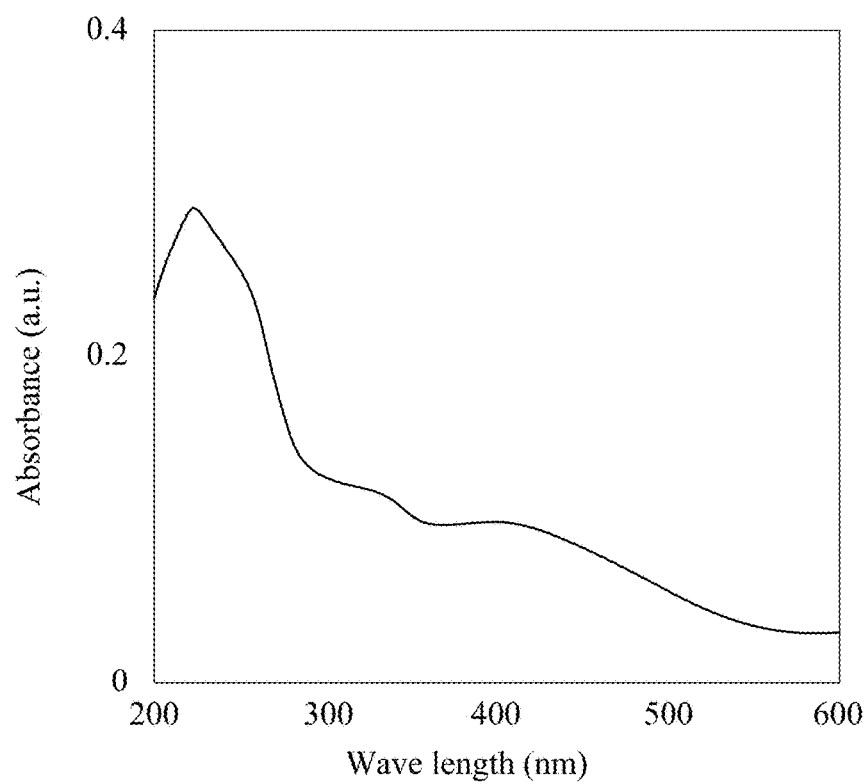
FIG. 9I shows DRS-UV and schematic presentation of IAUM-56 prepared in NSS
Figure 9J:
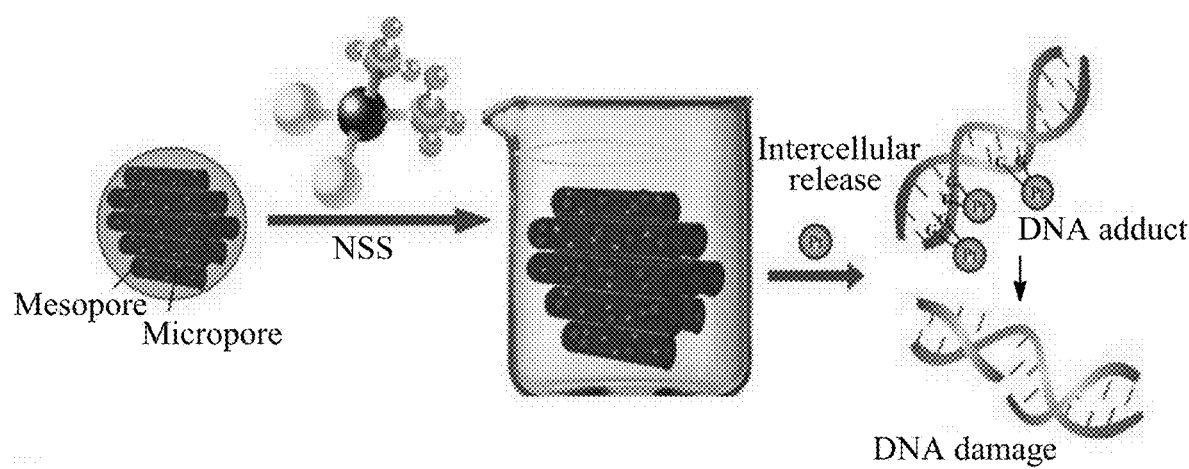
FIG. 9J shows schematic presentation of IAUM-56 prepared in NSS.

In order to investigate the solvent effect (DMSO and NSS) over the present nanocarriers, morphological differences of parent supports SiMCM-41, mesosilicalite, and nanoformulations cisplatin/SiMCM-41 (IAUM-35) and cisplatin/mesosilicalite (IAUM-34) in DMSO and cisplatin/SiMCM-41 (IAUM-55) and cisplatin/mesosilicalite (IAUM-56) in NSS are investigated using TEM analysis (FIGS. 8a-8f). The coordination of platinum in cisplatin over SiMCM-41 and mesosilicalite loaded in DMSO and NSS are examined using diffuse reflectance UV-Visible spectroscopy and the schematic representation of solvent effect for cisplatin deposition over mesosilicalite are shown in FIGS. 8g-8j, respectively. The TEM image of parent SiMCM-41 is seen through perpendicular electron beam and shows uniform arrangement of hexagonal pore nanochannels indicating uniform porosity of mesophase (FIG. 8a). In case of nanoformulations cisplatin/SiMCM-41 (IAUM-35) prepared in DMSO solvent, the formation of platinum nanoclusters are more clearly seen and are present as separate particle phase in cluster/agglomerated form segregated partly over the silica support and outside the pore channels of nanocarriers (FIG. 8b). In contrast, cisplatin/SiMCM-41 nanocomposite in NSS shows different textural phenomenon, where the hexagonal textures is preserved and the deposition of cisplatin is well dispersed in nanoform (FIG. 8c). In case of the parent cisplatin/mesosilicalite, the perpendicular view shows the disruption of pore channels which indicates presence of disoriented hexagonal phase due to nanocomposite formation between microphase of silicalite and mesophase of SiMCM-41. The preparation of mesosilicalite through top-down approach using alkaline pH in presence of CTAB clearly shown to form the hierarchical pore structure. The appearance of such disorientation in the mesophase is primarily attributed to the zeolitic nanoclusters that become difficult to connect with mesophase (FIG. 8d). The presence of nanozeolitic phase is clearly visible with uneven nanozeolitic silicalite structure attached to the ordered mesochannels. Cisplatin over mesosilicalite in DMSO showed irregular texture with variation of thickness as seen through the bright and dark contrast. Unlike conventional SiMCM-41, no distinct separation of platinum nanoclusters is observed (FIG. 8e). In case of NSS, a clear hierarchical phase of composite formation is observed, while the absence of distinct agglomeration shows well dispersed platinum species in the probable range of 2 nm (FIG. 8f). Diffuse reflectance UV-Vis spectroscopy is used to detect the coordination aspect of platinum species over silica support [Ravat et al. "Platinum group metals substituted MCM-41 molecular sieves: Synthesis, characterization and application as novel catalysts for the reduction of NO by CO", *J Mol Catal A Chem.* 2009, 314, 49-54—incorporated herein by reference]. In case of cisplatin-DMSO interactions, earlier study has shown that the modification of platinum occurs through ligand replacement by DMSO. Through electrospray ionization mass spectra technique, six different species of cisplatin complexes was determined. The chloride anion ligand replacement was found to be major cause for platinum(II) complex deactivation [Hall et al. Basis for design and development of Platinum(IV) anticancer complexes. *J Med Chem.* 2007, 50, 3403-3411—incorporated herein by reference]. The diffuse reflectance spectra of IAUM-35 (cisplatin/SiMCM-41) prepared in DMSO and IAUM-56 (cisplatin/mesosilicalite) prepared in normal saline are shown in FIGS. 8g and 8i, respectively. IAUM-35 has one intense broad absorption maximum at about 226 nm and extends to 350 nm (see FIG. 8g). In case of IAUM-56 prepared in normal saline solvent, a less intense and distinct absorption maximum at 224 nm is observed due to tetrahedron configuration in addition to two well pronounced additional maxima at about 320 nm and 410 nm indicating the presence of octahedral coordinated platinum species as nanoclusters or aggregates (see FIG. 8i). Compared to DMSO, the absorption bands of IAUM-56 significantly reduced indicating existence of different types of platinum species. The presence of UV bands at 260-335 nm is reported due to the presence of atomic sized nanoclusters of platinum [Wojtaszek-Gurdak et al. "The role of pillaring in MCM-22 on the dispersion of noble metals and catalytic" *Materials Research Bulletin* 2016, 76, 169-178—incorporated herein by reference]. So, the presence of such peak for IAUM-35 shows the electrons transition between molecular orbitals of platinum nanoclusters. In particular, electron charge transfer of tetrahedrally coordinated Platinum(IV) species is predominant in the network of hexagonal mesophase. The formation of different nano sized metal particles in dispersed or aggregated forms are reported to occur through hydration process. The presence of large surface energy of nanometal particles in colloidal state tends to form aggregations. However, the size and shape of platinum nanoparticles can be controlled, which depends on the platinum source, stabilizers (capping agent), and reaction conditions such as synthesis time, temperature and solvents used. The electrostatic repulsion exerted by solvent ions over nanoparticles decreases the surface energy of nanoparticles and thereby stabilizes the small particles in colloidal state [Cardenas-Trivino et al. "Living colloidal palladium in non-aqueous solvents. Formation, stability, and film-forming properties. Clustering of metal atoms in organic media" *Langmuir* 1987, 3, 986—incorporated herein by reference]. In particular, the controlling process of metal nanocluster formation becomes at high metal concentration. The presence of ethylene glycol or any other simple ions like hydroxides in colloidal solution are reported to act as a stabilizer. The process of aggregation and coalescence are reported to be subdued due to potential barrier created by the stabilizer leading to formation of nanoclusters of uniform sizes [Wang et al. "Solvent and Simple Ion-Stabilized Metal Nanoclusters: Chemical Synthesis and Application; Chapter 19, Metal Nanoclusters in Catalysis and Materials Science, *The issue of Size Control,* 2008, 327-340—incorporated herein by reference]. Compared to normal saline, the presence of six-fold intense absorption band of platinum in DMSO (FIG. 8g) shows that interaction between platinum-platinum t is more favored (FIG. 8b) than platinum-mesosilicalite interactions. The study shows that normal saline solution tends to favor different type of platinum species irrespective of the nanocarrier (either SiMCM-41 or mesosilicalite). The presence of strong bands of tetrahedral along with octahedral species indicating dispersion and interaction of platinum occurs more on the mesosilicalite support which are further supported by TEM analysis (FIGS. 8c and 8f).

Based on the characterization and MTT assay, the important role played by the solvent for cisplatin dispersion and cell inhibitory activity are shown as schematic representation (FIGS. 8h and 8j). The preparation of cisplatin/nanocarrier formulation in DMSO forms tetrahedrally bound platinum nanoclusters, while NSS is found to effectively transform the crystalline form of cisplatin into nanoform and disperse it well over mesosilicalite as different platinum species. In case of normal saline with 0.9% NaCl solution, the presence of alkaline condition is proposed to form the suspension or colloid of platinum nanoparticles. Cisplatin based drugs are reported to be activated through solvent interactions by the process of "aquation". The displacement of chloride ligand by water present inside the cell is termed as important step for cell entry [Knox et al. Mechanism of cytotoxicity of anticancer platinum drugs: evidence that cis-diamminedichloroplatinum(II) and cis-diammine-(1,1-cyclobutanedi-carboxylato)platinum(II) differ only in the kinetics of their interaction with DNA. *Cancer Res.* 1986, 46, 1972-1979—incorporated herein by reference]. The presence of saline containing 0.9% NaCl is shown to exert a positive influence over cisplatin and retains the chloride anion [Hall et al. "Dimethyl sulfoxide Inactivates Cisplatin, Carboplatin and Other Platinum Complexes. *Cancer Res.* 2014, 74(14), 3913-3922—incorporated herein by reference]. FIGS. 5-7 show that cisplatin/mesosilicalite prepared using normal saline exerts high cell inhibitory effect. In the present preparation, the use of normal saline as solvent for cisplatin loading over mesosilicate is an important factor to stabilize nanotranformed cisplatin, wherein the chloride ion of normal saline stabilizes the chloride ligand of cisplatin. The nanoform of cisplatin is present due to the large surface to volume ratio. Several platinum(II) complexes may be adsorbed on the surface of mesosilicalite that eventually aids cisplatin diffusion into the cells effectively by replacing chloride ion with water leading to high cell inhibitory effect.

The present disclosure describes the preparation of robust hierarchical mesosilicalite nanocarrier using top-down approach. Rather than mere physical mixture, the presence of interlinked micro and mesophase was proven effective in drug release study. The development of cisplatin/mesosilicalite nanoformulation (IAUM-56) in normal saline is disclosed for cancer therapy. The use of normal saline solution to load cisplatin on the nanocarrier is shown to produce substantially more effective drug than that when DMSO is used to load the cisplatin.

The invention claimed is:

1. A mesosilicalite nanocarrier, comprising:
  a hierarchical silicalite having a silica to aluminum molar ratio in a range of 1000:1 to 3000:1, comprising:
  a mesophase with mesopores of a hexagonal structure; and
  a microphase with micropores of a microporous volume in the range of 0.05 cc/g to 0.1 cc/g; and
  a platinum(II) complex loaded in the mesopores and micropores of the nanocarrier;
  wherein a mean pore diameter of the mesosilicalite nanocarrier is in the range of 1.5 nm to 5.5 nm and wherein the nanocarrier has a pore size distribution comprising micropores having a pore diameter in the range of 2.0-2.8 nm and mesopores having a pore diameter in the range of 2.9-4.0 nm.

2. The mesosilicalite nanocarrier of claim 1, wherein the platinum(II) complex is at least one selected from the group consisting of cisplatin, carboplatin, oxaliplatin, nedaplatin, triplatin tetranitrate, phenanthriplatin, picoplatin, and strataplatin.

3. The mesosilicalite nanocarrier of claim 1, wherein the platinum(II) is present in amount in the range of 0.001 to 1800 mmol/g of the total weight of the mesosilicalite nanocarrier.

4. The mesosilicalite nanocarrier of claim 1, wherein the platinum(II) is present in amount in the range of 0.01 to 0.9 mmol/g of the total weight of the mesosilicalite nanocarrier.

5. The mesosilicalite nanocarrier of claim 1, wherein the mesosilicalite nanocarrier has a surface area in the range of 400 to about 1400 $m^2/g$.

6. The mesosilicalite nanocarrier of claim 1, wherein the mesosilicalite nanocarrier has a pore volume in the range of 0.30-0.90 mL/g.

7. A pharmaceutical composition comprising the mesosilicalite nanocarrier of claim 1.

8. The pharmaceutical composition of claim 7, wherein the platinum(II) complex is at least one selected from the group consisting of cisplatin, carboplatin, oxaliplatin, nedaplatin, triplatin tetranitrate, phenanthriplatin, picoplatin, and strataplatin.

9. The pharmaceutical composition of claim 7, wherein the platinum(II) complex is cisplatin.

10. The pharmaceutical composition of claim 7, wherein the mesosilicalite nanocarrier loaded with the platinum(II) complex at a loading of in the range of about 0.011 to mmol of 0.9 mmol of platinum(II) complex per gram of nanocarrier.

11. The pharmaceutical composition of claim 7, further comprising a chemotherapeutic agent.

12. The pharmaceutical composition of claim 7, further comprising one or more carriers and/or excipients selected from the group consisting of a buffer, an inorganic salt, a fatty acid, a vegetable oil, a synthetic fatty ester, a surfactant, a sugar, a polymer, and combinations thereof.

* * * * *